United States Patent [19]
Vuori et al.

[11] Patent Number: 5,830,504
[45] Date of Patent: Nov. 3, 1998

[54] COOPERATIVE COMBINATIONS OF LIGANDS CONTAINED WITHIN A MATRIX

[75] Inventors: Kristiina Vuori, San Diego; Erkki I. Ruoslahti, Rancho Santa Fe, both of Calif.

[73] Assignee: La Jolla Cancer Research Foundation, La Jolla, Calif.

[21] Appl. No.: 456,878

[22] Filed: Jun. 1, 1995

Related U.S. Application Data

[63] Continuation of Ser. No. 347,942, Nov. 30, 1994, which is a continuation-in-part of Ser. No. 176,999, Jan. 3, 1994, abandoned, which is a continuation of Ser. No. 142,842, Oct. 25, 1993, abandoned, which is a continuation of Ser. No. 978,054, Nov. 18, 1992, abandoned, which is a continuation of Ser. No. 286,973, Dec. 20, 1988, abandoned.

[51] Int. Cl.$^6$ .......................... A61K 38/04; A61K 38/18; A61K 38/20; A61K 38/28

[52] U.S. Cl. ............................ 424/484; 424/486; 514/2; 514/3

[58] Field of Search .................................. 514/2, 3, 4, 8, 514/12, 13, 23; 424/484, 486, 488

[56] References Cited

U.S. PATENT DOCUMENTS

| | | | |
|---|---|---|---|
| 3,883,393 | 5/1975 | Knazek et al. | 435/240.242 |
| 4,511,653 | 4/1985 | Play et al. | 435/68.1 |
| 4,517,686 | 5/1985 | Ruoslahti et al. | 623/1 |
| 4,578,079 | 3/1986 | Ruoslahti et al. | 623/11 |
| 4,589,881 | 5/1986 | Ruoslahti et al. | 623/11 |
| 4,636,524 | 1/1987 | Balazs et al. | 514/781 |
| 4,661,111 | 4/1987 | Ruoslahti et al. | 623/11 |
| 4,683,291 | 7/1987 | Zimmerman et al. | 530/324 |
| 4,703,108 | 10/1987 | Silver et al. | 530/356 |
| 4,760,131 | 7/1988 | Sundsmo et al. | 530/356 |
| 4,857,508 | 8/1989 | Adams et al. | 514/18 |
| 4,874,746 | 10/1989 | Antoniades et al. | 514/21 |
| 4,885,163 | 12/1989 | Shear et al. | 514/2 |
| 4,973,466 | 11/1990 | Reich | 424/426 |
| 4,983,580 | 1/1991 | Gibson et al. | 514/2 |
| 5,053,388 | 10/1991 | Gibson et al. | 514/2 |
| 5,120,829 | 6/1992 | Pierschbacher et al. | 530/326 |
| 5,128,326 | 7/1992 | Balazs et al. | 514/54 |
| 5,196,185 | 3/1993 | Silver et al. | 424/45 |

FOREIGN PATENT DOCUMENTS

| | | |
|---|---|---|
| 142192 | 5/1984 | European Pat. Off. |
| 282317 A2 | 3/1988 | European Pat. Off. |
| 341915 | 11/1989 | European Pat. Off. |
| 562862 A1 | 3/1993 | European Pat. Off. |
| 574880 A1 | 6/1993 | European Pat. Off. |
| 578083 A3 | 6/1993 | European Pat. Off. |
| 63-264069 | 10/1988 | Japan |
| 1-279836 | 11/1989 | Japan |
| 6-80694 | 6/1994 | Japan |
| 88/03151 | 5/1988 | WIPO |
| 88/03810 | 6/1988 | WIPO |

OTHER PUBLICATIONS

Schwartz, M.A., "Transmembrane signalling by intergrins" *Trends Cell Biol.* 2:304–308 (1992).

Schaller and Parson, "Focal adhesion kinase: an integrin--linked protein tyrosine kinase" *Trends Cell Biol.* 3:258–262 (1993).

Keller and Lienhard, "Insulin signalling: the role of insulin receptor substrate 1" *Trends Cell Biol.* 4:115–119 (1994).

Burridge et al., "Signals from focal adhesions" *Curr. Biol.* 2(10):537–539 (1992).

Buratowski, S., "The Basics of Basal Transcription by RNA Polymerase II" *Cell* 77:1–3 (1994).

Hynes, R.O., "Integrins: Versatility, Modulation, and Signaling in Cell Adhesion" *Cell* 69:11–25 (1992).

Albelda and Buck, "Integrins and other cell adhesion molecules" *FASEB J.* 4:2868–2880 (1990).

Juliano and Haskill, "Signal Transduction from the Extracellular Matrix" *J. Cell. Biol.* 3:577–585 (1993).

Chun and Jacobson, "Requirement for Diacylglycerol and Protein Kinase C in HeLa Cell–Substratum Adhesion and Their Feedback Amplification of Arachidonic Acid Production for Optimum Cell Spreading" *Mol. Biol. Cell* 4:271–281 (1993).

Morla et al., "Hematopoietic Growth Factors Activate the Tyrosine Phosphorylation of Distinct Sets of Protein in Interleukin–3–Dependent Murine Cell Lines" *Mol. Cell. Biol.* 8(5):2214–2218 (1988).

Pathak et al., "Rapid Photopolymerization of Immunoprotective Gels in contact with Cell and Tissue" *J. Am. Chem. Soc.* 114:8311–8312 (1992).

Schreiner et al., "Expression and role of integrins in adhesion of human colonic carcinoma cells to extracellular matrix components" *Clin. Expl. Metastasis* 9(2):163–178 (1991).

Grinnell, F., "The Role of Fibronectin in the Bioreactivity of Material Surfaces" in: *Biocompatible Polymers, Metals, and Composites* (Ed. M. Szycher), Technomic Publishing Co., Lancaster, Pennsylvania (1983).

Wang et al., "Common elements in interleukin 4 and insulin signaling pathways in factor–dependent hematopoietic cells" *PNAS USA* 90:4032–4036 (1993).

Polarek et al., "Development of a Provisional Extracellular Matrix to Promote Wound Healing" *Wounds* 6(2):46–53 (1994).

(List continued on next page.)

*Primary Examiner*—John Ulm
*Assistant Examiner*—Kare E. Brown
*Attorney, Agent, or Firm*—Campbell & Flores LLP

[57] ABSTRACT

The present invention provides compositions and methods for promoting cell migration and tissue regeneration. The composition contains a ligand for the $\alpha_v\beta_3$ integrin and a ligand for the insulin receptor, the PDGF receptor, the IL-4 receptor, or the IGF receptor, combined in a matrix. The combination of $\alpha_v\beta_3$ ligand and growth factor produces an unexpected synergistic effect in enhancing wound healing compared with the effect of each component separately. The present invention also provides a method of wound healing and a method of inducing tissue regeneration by applying the compositions of the present invention to the site of the wound.

4 Claims, 6 Drawing Sheets

OTHER PUBLICATIONS

Wethers et al., "Accelerated Healing of Chronic Sickle–Cell Leg Ulcers Treated With RGD Peptide Matrix" *Blood* 84(6):1775–1779 (1994).

Steed et al., "Promotion and Acceleration of Diabetic Ulcer Healing by Arginine–Glycine–Aspartic Acid (RGD) Peptide Matrix" *Diabetic Care* 18:39–46 (1995).

Jyung et al., "Increased wound–breaking strength induced by insulin–like growth factor I in combination with insulin––like growth factor binding protein–1" *Surgery* 115(2):233–239 (1994).

Robson et al., "Recombinant Human Platelet–derived Growth Factor–BB for the Treatment of Chronic Pressure Ulcers" *Ann. Plastic Surgery* 29(3):193–201 (1992).

Lynch et al., "Role of platelet–derived growth factor in wound healing: Synergistic effects with other growth factors" *PNAS USA* 84:7696–7700 (1987).

Khouri et al., "Tissue generation with growth factors" *Surgery* 114(2):374–380 (1993).

Pierce et al., "In Vivo Incisional Wound Healing Augmented by Platelet–derived Growth Factor and Recombinant c–sis Gene Homodimeric Proteins" *J. Exp. Med.* 167:974–987 (1988).

Mustoe et al., "A Phase II Study to Evaluate Recombinant Platelet–Derived Growth Factor–BB in the Treatment of Stage 3 and 4 Pressure Ulcers" *Arch. Surg.* 129:213–219 (1994).

Pierce et al., "Role of Platelet–Derived Growth Factor in Wound Healing" *J. Cell. Biochem.* 45:319–326 (1991).

Mueller et al., "The Effect of Insulinlike Growth Factor I on Wound Healing Variables and Macophages in Rats" *Arch. Surg.* 129:262–264 (1994).

Pierschbacher et al., "Manipulation of Cellular Interactions with Biomaterials Toward a Therapeutic Outcome: A Perspective" *J. Cell. Biochem.* 56:150–154 (1994).

Hayashi et al., "Expression and Functional of Chicken Integrin $\beta 1$ Subunit and its Cytoplasmic Domain Mutants in Mouse NIH 3T3 Cells" *J. Cell Biol.* 110:175–184 (1990).

Hayman et al., "Detachment of Cells from Culture Substrate by Soluble Fibronectin Peptides" *J. Cell Biol.* 100:1948–1954 (1985).

Wayner et al., "Integrine $\alpha v \beta 3$ and $\alpha v \beta 5$ Contribute to Cell Attachment to vitronectin but Differentially Distribute on the Cell Surface" *J. Cell Biol.* 113(4):919–929 (1991).

Leavesley et al., "Requirement of the Integrin $\beta 3$ Subunit for Carcinoma Cell Spreading or Migration on Vitronectin and Fibrinogen" *J. Cell Biol.* 117(5):1101–1107 (1992).

Argraves et al., "Amino Acid Sequence of the Human Fibronectin Receptor" *J. Cell Biol.* 105:1183–1190 (1987).

Schubert and Kimura, "Substratum–Growth Factor Collaborations Are Required for the Mitogenic Activities and FGF on Embryonal Carcinoma Cells" *J. Cell Biol.* 114(4):841–846 (1991).

Lillien et al., "Extracellular Matrix–associated Molecules Collaborate with Ciliary Neurotrophic Factor to Induce Type–2 Astrocyte Development" *J. Cell Biol.* 111:635–644 (1990).

Frisch and Francis, "Disruption of Epithelial Cell–Matrix Interactions Induces Apoptosis" *J. Cell. Biol.* 124(4):619–626 (1994).

Plow et al., "The effect of Arg–Gly–Asp–containing peptides on fibrinogen and von Willebrand factor binding to platelets" *PNAS USA* 82:8057–8061 (1985).

Pierschbacher et al., "Synthetic peptide with cell attachment activity of fibronectin" *PNAS USA* 80:1224–1227 (1983).

Pytela et al., "A 125/115–kDa cell surface receptor specific for vitronectin itneracts with the arginine–glycine–aspartic acid adhesion sequence derived from fibronectin" *PNAS USA* 82:5766–5770 (1985).

Rose et al., "Insulin receptor substrate 1 is required for insulin–mediated mitogenic signal transduction" *PNAS USA* 91:797–801 (1994).

Suzuki et al., "cDNA and amino acid sequence of the cell adhesion protein receptor recognizing vitronectin reveal a transmembrane domain and homologies with other adhesion protein receptors" *PNAS USA* 83:8614–8618 (1986).

Buckley et al., "Sustained release of epidermal growth factor accelerates wound repair" *PNAS USA* 82:7340–7344 (1985).

Kornberg et al., "Signal transduction by integrins: Increased protein tyrosine phosphorylation caused by clustering of $\beta 1$ integrins" *PNAS USA* 88:8392–8396 (1991).

Engvall et al., "Monhelical, Fibronectin–Binding Basement– Membrane Collagen from Endodermal Cell Culture" *Cell* 29:475–482 (1982).

Cheresh et al., "A Novel Vidtronectin Receptor Integrin ($\beta v \beta x$) is Responsible for Distinct Adhesive Properties of Carcinoma Cells" *Cell* 57:59–69 (1989).

Ruoslahti and Pierschbacher, "Arg–Gly–Asp: A Versatile Cell Recognition Signal" *Cell* 44:517–518 (1986).

Vuori and Ruoslahti, "Activation of Protein Kinase C Precedes $\alpha 5 \beta 1$ Integrin–mediated Cell Spreading on Fibronectin" *J. Biol. Chem.* 268(29):21459–21462 (1993).

Ruoslahti and Pierschbacher, "New Perspectives in Cell Adhesion: RGD and Integrins" *Science* 238:491–497 (1987).

Springer, T.A., "Adhesion receptors of the immune system" *Nature* 346:425–434 (1990).

Sun et al., "Structure of the insulin receptors substrate IRS–1 defines a unique signal transduction protein" *Nature* 352:73–77 (1991).

McClain et al., "A Mutant Insulin Receptor with Defective Tyrosine Kinase Displays No Biologic Activity and Does Not Undergo Endocytosis" *J. Biol. Chem.* 262(30):14663–14671 (1987).

Koivunen et al., "Selection of Peptides Binding to the $\alpha 5 \beta 1$ Integrin from Phage Display Library" *J. Biol. Chem.* 268(27):20205–20210 (1993).

Bartfeld et al., "The $\alpha v \beta 3$ integrin Associates with a 190–kDa Protein That is Phosphorylated on Tyrosine in Response to Platelet–derived Growth Factor" *J. Biol. Chem.* 268:17270–17276 (1993).

White and Kahn, "The Insulin Signaling System" *J. Biol. Chem.* 269(1):1–4 (1994).

Kadowaki et al., "Insulin–like Growth Factors, Insulin, and Epidermal Growth Factor Cause Rapid Cytoskeletal Reorganization in KB Cells" *J. Biol. Chem.* 261(34):16141–16147 (1986).

Shah et al., "Control of scarring in adult wounds by neutralising antibody to transforming growth factor $\beta$" *Lancet* 339:213–214 (1992).

Ruoslahti et al., "Interaction of Fibronectin with Antibodies and Collagen in Radioimmunoassay" *Biochimica Biophysica Acta* 534:210–218 (1978).

Pierce et al., "Platelet–derived Growth Factor–BB and Transforming Growth Factor Betal Selectively Modulate Glycosaminoglycans, Collagen, and Myofibroblasts in Excisional Wounds" *Am. J. Path.* 138(3):629–646 (1991).

Stracke et al., "Insulin–like growth factors stimulate chemotaxis in human melanoma cells" *Biochem. Biophys. Res. Commun.* 153(3):1076–1083 (1988).

Ruoslahti, E., "Integrins" *J. Clin. Invest.* 87:1–5 (1991).

Meredith et al., "The Extracellular Matrix as a Cell Survival Factor" *Mol. Biol. Cell* 4:953–961 (1993).

Mellstrom et al., "The effect of platelet–derived growth factor on morphology and motility of human glial cells" *J. Muscle Res. Cell Motil.* 4:589–609 (1983).

Zhang et al., "The αvβ1 Integrin Functions as a Fibronectin Receptor But Does Not Support Fibronectin Matrix Assembly and Cell Migration on Fibronectinl" *J. Cell Biol.* 122(1):235–242 (1993).

Pytela et al., "Arginine–Glycine–Aspartic Acid Adhesion Receptors" *Meths. Enzymol.* 144:475–489 (1987).

von Schroeder et al., "The use of polylactic acid matrix and periosteal grafts for the reconstructions of rabbit knee articular" *J. Biomed. Mats. Res.* 25:329–339 (1991).

Myers and White, "The New Elements of Insulin Signaling, Insulin Receptor Substrate–1 and Proteins with SH2 Domains" *Diabetes* 42:643–650 (1993).

Engvall et al., "Affinity Chromatography of Collagen on Collagen–Binding Fragments of Fibronectin" *Collagen Rel. Res.* 1:505–516 (1981).

Ruslahti et al., "Fibronectin: Current Concepts of its Structure and Functions" *Coll. Res.* 1:95–128 (1981).

Sastry and Horwitz, "Integrin cytoplasmic domains: mediators of cytoskeletal linkages and extra– and intracellular initiated transmembrane signaling" *Curr. Opin. Cell Biol.* 5:819–831 (1993).

Ginsberg et al., "Inside–out integrin signalling" *Curr. Opin. Cell Biol.* 4:766–771 (1992).

Goa and Benfield, "Hyaluronic Acid, A Review of its Pharmacology and Use as a Surgical Aid in Ophthalmology, and its Therapeutic Potential in Joint Disease and Wound Healing" *Drugs* 47(3):536–566 (1994).

Bockus and Stiles, "Regulation of Cytoskeletal Architecture by Platelet–Derived Growth Factor, Insulin and Epidermal Growth Factor" *Exper. Cell Res.* 153:186–197 (1984).

Guan et al., "Fibronectin/integrin interaciton induces tryosine phosphorylation of a 120–kDa protein" *Cell Regulation* 2:951–964 (1991).

Stoker et al., "Anchorage and growth regulation in normal and virus–transformed cells" *Int. J. Cancer* 3:683–693 (1968).

Engvall and Ruoslahti, "Binding of soluble form of fibroblast surface protein, fibronectin, to collagen" *Int. J. Cancer* 20:1–5 (1977).

Schlessinger and Geiger, Epidermal growth factor induces redistribution of actin and α–actinin in human epidermal carcinoma cells, *Eper. Cell Res.* 134:273–279 (1981).

Neville et al., "Anti–T cell immunotxins: a look at post–endocytotic receptor–mediated routing" *J. Controlled Rel.* 24:133–144 (1993).

Hynes et al., "Fibronectins: Multifunctional modular glycoproteins" *J. Cell. Biol.* 95:369–377 (1982).

Petersen et al., "Partial primary structure of bovine plasma fibronectin: Three types of internal homology" *Proc. Natl. Acad. Sci.* 80:137–141 (1983).

Grinnell, F., "Cell attachment and spreading factors" in *Growth and Maturation Factors* (Dr. Gordon Guroff, Ed.) John Wiley & Sons, Inc., (1983).

Grinnell, G., "The role of fibronectin in the bioreactivity of material surfaces" in *Biocompatible Polymers, Metal, and Composites* (Ed. Michael Szycher), Technomic Publishing, Lancaster, Pennsylvania (1983).

Hayashi et al., "Domain structure of the carboxyl–terminal half of human plasma fibronectin" *J. Biol. Chem.* 258:3332–3340 (1983).

Kornblihtt, et al., "Isolation and characterization of cDNA clones in human and bovine fibronectins" *Proc. Natl. Acad. Sci.* 80:3218–3222 (1983).

McDonagh et al., "Amino acid sequence of the factor XIII$_a$ acceptor site in bovine plasma fibronectin," *Febs Letters* 127:174–178(1981).

Ruoslahti et al., "Alignment of biologically active domains in the fibronectin molecule," *J. Biol. Chem.* 256:7277–7281 (1981).

Pande et al., "Comparative structural studies of human plasma and amniotic fluid fibronectins," *Bioch. Biophy. Res. Comm.* 101:265–272 (1981).

Pande et al., "$NH_2$–terminal sequences of DNA–, heparin–, and gelatin–binding tryptic fragments from human plasma fibronectin," *Arch. Bioch. Biophy.* 213:258–258 (1982).

Pierschbacher et al., "The cell attachment domain of fibronectin," *J. Biol. Chem.* 257:9593–9597 (1982).

Seitz et al., "Effect of fibronectin on the adhesion of an established cell line to a surface reactive biomaterial," *J. Biomed. Mat. Res.* 16:195–207.

Vibe–Pedersen et al., "Amino acid sequence of a peptide from bovine plasma fibronectin containing a free sulfhydryl group (cysteine)," *Febs. Letters* 142:26–30 (1982).

Sekiguchi et al., "Monoclonal antibodies directed to two different domains of human plasma fibronectin: Their specificities", *Fed. Eur. Bich. Soc.* 142:243–246 (1982).

Ehrismann et al., "Arrangement of attachment–promoting, self–association, and heparin–binding sites in horse serum fibronectin", *J. Biol. Chem.* 257:7381–7387 (1982).

Clark et al., "Fibronectin is produced by blood vessels in response to injury", *J. Exp. Med.* 156:646–651 (1982).

Engvall et al., "Affinity chromatography of collagen on collagen–binding fragments of fibronectin" *Collagen Rel. Res.* 1:505–516 (1981).

Hynes, R.O., "Fibronectins: A family of complex and versatile adhesive glycoproteins derived from a single gene", The Harvey Lectures, Series 81, at p. 134 (1987).

Lam et al., "Evidence that arginyl–glycyl–aspartate peptides and fibrinogen α chain peptides share a common binding site on platelets" *J. Biol. Chem.* 262:947 (1987), Grinnell et al., *Cell* 19:517–252 (1980).

Bernard et al., *Biochem.* 22:5213–5223 (1983).

Kohno et al., *J. Biol. Chem.* 259(22):13668–13673 (1984).

Seyer et al., *Biochem.* 20:2621–2627 (1981).

Babel et al., *Euro J. Biochem.* 143:545–556 (1984).

Hynes et al., "Cell surface fibronectin and oncogenic transformation," *J. Supramolecular Structure* 11:95–104 (1979).

Hahn et al. "Isolation and biological characterization of active fragments of the adhesive glycoprotein fibronectin," *Cell* 18:1043–1051 (1979).

Sekiguchi et al., "Fuctional domain structure of fibronectin," *Proc. Natl. Acad. Sci.* 77:2661–2665 (1980).

Grinnell et al., "Distribution of fibronectin during wound healing in Vivo," *J. Invest. Dermatol.* 76:181–189 (1981).

Danilov et al., *Expt. Cell Res.* 182:186–196 (1989).

Pierschbacher et al., *Nature* 309:30–33 (1984).

Pytela et al., *Science* 31:1559–1561 (1986).

Singer et al., *J. Cell Biol.* 104:573–584 (1987).

Suzuki et al., *J. Biol. Chem.* 262(29):14080–14085 (1987).

Plow et al., *Proc. Natl. Acad. Sci. (USA)* 82:8057–8061 (1985).

Mustoe et al., Accelerated Healing of Incisional Wounds in Rats Induced by Transfoming Growth Factor–Beta, Science 1333–1336 (1987).

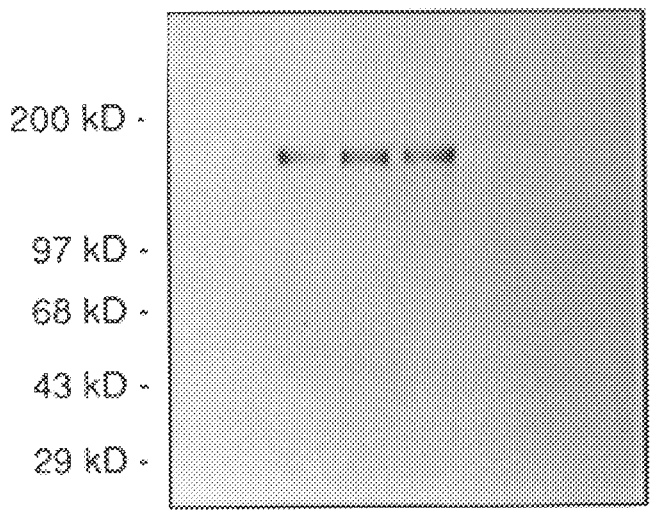
FIG. 1A
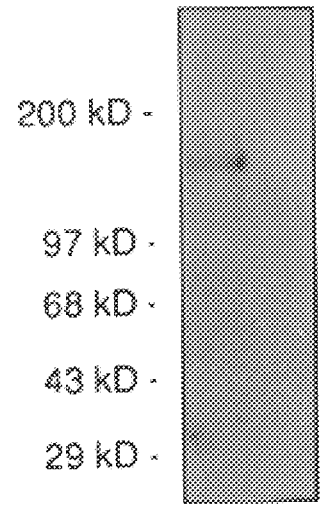
FIG. 1B
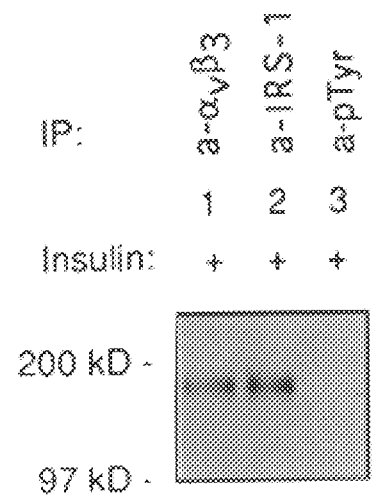
FIG. 1C
FIG. 1D

SEQUENCE LISTING ( 1 ) GENERAL INFORMATION:

( i i i ) NUMBER OF SEQUENCES: 3

(2) INFORMATION FOR SEQ ID NO:1:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 2..6
        (D) OTHER INFORMATION: /note= "X=(dR), WHICH IS THE D ISOMER OF ARGININE"

(ix) FEATURE:
        (A) NAME/KEY: Peptide
        (B) LOCATION: 10
        (D) OTHER INFORMATION: /note= "X=(dR), WHICH IS THE D ISOMER OF ARGININE"

(xi) SEQUENCE DESCRIPTION: SEQ ID NO:1:

```
Gly Xaa Xaa Xaa Xaa Xaa Gly Gly Gly Xaa Gly Asp Ser Pro Ala Ser
1               5                       10                  15
Ser Lys
```

(2) INFORMATION FOR SEQ ID NO:2:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:2:

```
Gly Arg Gly Asp Ser Pro Lys
1               5
```

(2) INFORMATION FOR SEQ ID NO:3:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:3:

```
Gly Arg Gly Glu Ser Pro Lys
1               5
```

COOPERATIVE COMBINATIONS OF LIGANDS CONTAINED WITHIN A MATRIX

RELATED APPLICATIONS

This application is a continuation of application Ser. No. 08/347,942, filed Nov. 30, 1994, which is a continuation-in-part of application Ser. No. 08/176,999, filed Jan. 3, 1994, now abandoned, which is incorporated herein by reference, and which is a continuation of application Ser. No. 08/142,842, filed Oct. 25, 1993, now abandoned, which is a continuation of application Ser. No. 07/978,054, filed Nov. 18, 1992, now abandoned, which is a continuation of application Ser. No. 07/286,973, filed Dec. 20, 1988, now abandoned.

ACKNOWLEDGMENT

This invention was made in part with Government support under National Cancer Institute Grants CA 42507, CA 28896 and Cancer Center Support Grant CA 30199. Therefore, the Government may have certain rights in the invention.

BACKGROUND OF THE INVENTION

The present invention relates to compositions and methods for enhancing cell growth and tissue regeneration in the wound healing process.

Slow wound healing, inappropriate wound healing, or lack of healing represent serious medical problems affecting millions of individuals. These problems occur in dermal wounds such as decubitus ulcers, severe burns and diabetic ulcers and eye lesions including dry eye and corneal ulcer, as well as surgical wounds, and other pathologies.

In the wound healing process, tissue is replaced through the migration of cells and the synthesis of extracellular matrix by these cells. This repair process requires that the correct type of cell migrate into the wound in sufficient numbers to have a healing effect: macrophages to debride wounds, fibroblasts for the formation of extracellular matrix components in wounds where the extracellular matrix was damaged, capillary endothelial cells to promote angiogenesis and provide the blood supply, and epithelial cells to ultimately cover the wound.

The unwounded dermis owes much of its structure and strength to interaction of cells with the extracellular matrix. The matrix contains proteins known to support the attachment of a wide variety of cells; fibronectin, vitronectin, thrombospondin, collagens and laminin are examples of matrix proteins. Plasma fibronectin deposition, for example, occurs at the wound site soon after wounding, although fibronectin is found in low concentrations in unwounded skin.

In addition to providing a scaffold for cell attachment and migration during wound healing, extracellular matrices also direct cellular proliferation and differentiation. Thus, matrix influences healing of a tissue in such a way that the correct tissue geometry is restored. When applied to wounds, exogenous fibronectin results in increased wound healing, epithelial migration and collagen deposition. However, fibronectin and other extracellular matrix proteins are less than ideal for treatment due to cost, availability and instability. In addition, as blood-derived products, extracellular matrix proteins may be vectors for infectious disease.

Cell growth factors, such as platelet derived growth factor (PDGF), fibroblast growth factor (FGF) or epidermal growth factor (EGF) also have been used to promote healing of dermis. However, growth factors primarily affect cell proliferation, when used alone, they do not confer the correct geometry of the new tissue, and can lead to overly vascularized tissue and abnormal healing. Moreover, it is known that an overabundance of growth factors such as TGF-β (transforming growth factor-β) and PDGF actually drive fibrosis, which in turn can impair successful healing. Additionally, many growth factors are known to be unstable and break down in topical or surface applications before a desired effect can be obtained.

Therefore, there remains a need for an effective agent to promote cell proliferation in association with cell attachment in the wound healing process.

SUMMARY OF THE INVENTION

The present invention provides compositions and methods for promoting cell migration and tissue regeneration. The composition contains a ligand for the $\alpha_v\beta_3$ integrin and a ligand for either the insulin receptor, the PDGF receptor, the IGF receptor, or the interleukin-4 (IL-4) receptor combined in a matrix. The combination of $\alpha_v\beta_3$ ligand and growth factor produces an unexpected synergistic effect in enhancing wound healing compared with the effect of each component separately. The present invention also provides a method of promoting wound healing and a method of inducing tissue regeneration by applying the compositions of the present invention to the site of the wound. In addition the compositions of the present invention are useful as matrices to support cell growth and tissue regeneration in vitro.

BRIEF DESCRIPTION OF THE DRAWINGS

FIG. 1A shows cell lysates of quiescent and insulin-stimulated HIRcB cells immunoprecipitated with various anti-integrin antibodies and immunoblotted with anti-phosphotyrosine antibody; FIG. 1B shows HIRcB cell lysates fractionated on GRGDSPK-Sepharose (SEQ ID NO: 2) and GRGESPK-Sepharose (SEQ ID NO: 3) immunoblotted with an antiphosphotyrosine antibody; FIG. 1C shows extracts from quiescent and insulin-stimulated HIRcB cells immunoprecipitated with anti-integrin antibodies and immunoblotted with anti-IRS-1 antibody; and FIG. 1D shows extracts of insulin-treated cells immunoprecipitated with various antibodies, then immunoblotted with antiphosphotyrosine antibodies.

DETAILED DESCRIPTION OF THE INVENTION

Figure 2A:
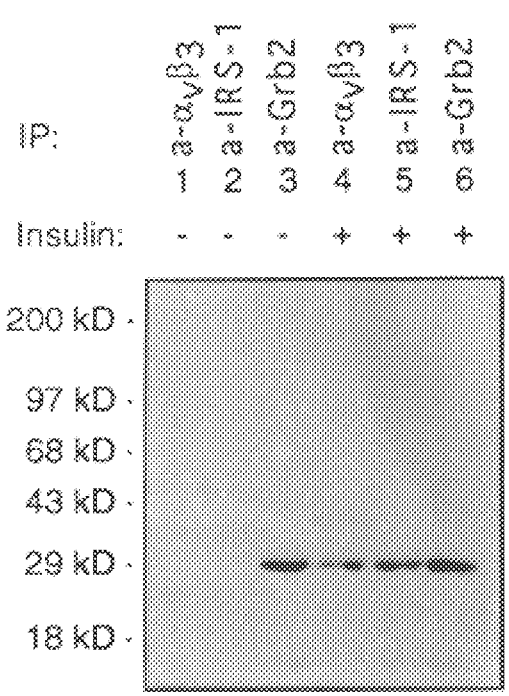
FIG. 2A shows quiescent and insulin-stimulated HIRcB cell extracts immunoprecipitated with various antibodies and immunoblotted with anti-Grb2 antibody.

The present invention provides a composition useful for promoting cell attachment, migration, and proliferation, and methods of using the composition to promote wound healing and tissue regeneration. The composition contains an $\alpha_v\beta_3$ integrin ligand and a growth factor receptor ligand combined within a matrix.

A Combination of Ligands

Adhesion of cells to extracellular matrix (ECM) is a prerequisite for cell proliferation and survival. (Stoker et al., *Int. J. Cancer* 3:683 (1968); Meredith et al., *Mol. Biol. Cell* 4:953 (1993); Frisch and Frances, *J. Cell Biol.* 124:619 (1994); Ruoslahti and Reed, *Cell* 77:1 (1994)). Adhesion of cells to extracellular matrix (ECM) is mediated mainly by integrins. (Ruoslahti, E., *J. Clin. Invest.* 87:1 (1991); Hynes, R. O., *Cell* 69:11 (1992)). Integrins are transmembrane receptors expressed on a wide variety of cells. There are eight known $\beta$ subunits and sixteen known $\alpha$ subunits which associate in different heterodimeric $\alpha\beta$ pairs to give more than 20 transmembrane glycoproteins with different ligand specificities, (Albelda and Buck, *FASEB J* 4:2868 (1990). Ruoslahti, *J. Clin. Invest.* 87:1 (1991), Hynes, *Cell* 69:11 (1992)). The ligands for several of the integrins are adhesive extracellular matrix proteins such as fibronectin, vitronectin, collagens and laminin. Many of the integrins recognize the sequence Arg-Gly-Asp in fibronectin and in a number of other adhesive proteins, as well as in synthetically derived peptides.

In some cases, cells must be adhered to the extracellular matrix in order for cells to respond to some growth factors. (Lilien et al. *J. Cell. Biol.* 111:635 (1990), Schubert and Kimura, *J. Cell. Biol.* 114:841 (1991)). Integrin-mediated cell adhesion and motility can be modulated by growth factors (Schlessinger and Geiger, *Exp. Cell Res.* 134:273 (1981); Bockus and Stiles, *Exp. Cell Res.* 153:186 (1984); Mellstrom et al., *J. Muscle Res. Cell Motil.* 4:589 (1983); Kadowaki et al., *J. Biol. Chem.* 261:16141 (1986); Stracke et al., *Biochem. Biophys. Res. Commun.* 153:1076 (1988)). For instance, growth factor treatment can disrupt focal adhesions, the presumed sites of integrin-mediated signaling (Schwartz, M. A., *Trends Cell Biol.* 2:304 (1992); Burridge et al., *Curr. Biol.* 2:537 (1992); Sastry and Horwitz, *Curr. Opin. Cell Biol.* 5:819 (1993); Juliano and Haskill, *J. Cell Biol.* 3:577 (1993)).

Integrins also mediate signals both from the exterior of the cell into the cell's interior (Juliano and Haskill, *J. Cell. Biol.* 120:577 (1993)), as well as from the inside out (Springer, *Nature* 346:425 (1990), Ginsberg, *Curr. Opin. Cell Biol.* 4:766 (1992)). these signals appear to play an important role in determining whether a cell lives or dies, proliferates, differentiates, migrates, invades tissues, or otherwise acts (Juliano and Haskill, *J. Cell. Biol.* 120:577 (1993), Ruoslahti and Reed, *Cell* 77:102 (1994)).

Tyrosine kinases and tyrosine phosphorylation play a role in cell signaling involving integrins. For example, an intracellular tyrosine kinase localized in focal adhesions (Focal Adhesion Kinase, FAK) is activated as a result of integrin ligation (Kornberg et al. *Proc. Natl. Acad. Sci. USA* 88:8392 (1991), Guan et al. *Cell Reg.* 2:951 (1991), Shaller and Parsons, *Trends Cell Biol* 3:258 (1993)). Protein kinase C (PKC) is also activated upon integrin ligation (Vuori and Ruoslahti, *J. Biol. Chem* 268:21459 (1993), Chun and Jacobson, *Mol. Biol. Cell* 4:271 (1993)). The activation of FAK and PKC appears to be a general response to integrin-mediated cell attachment.

The present invention is based on the discovery that growth factor receptor ligands in combination with ligands to integrins, particularly ligands to $\alpha_v$-containing integrins such as the $\alpha_v\beta_3$ integrin, enhance cell growth and tissue regeneration in a synergistic manner which exceeds the activity of each ligand separately. This has been demonstrated for a number of ligands, as described in the Examples below. For example, insulin, insulin-like growth factor (IGF), interleukin-4 (IL-4), and platelet-derived growth factor (PDGF), when combined with an $\alpha_v\beta_3$ ligand, such as vitronectin, enhance cell proliferation over that exhibited by cells in contact with only one of the ligands.

As demonstrated in the Examples given below, an unexpected link between $\alpha_v$ integrins and insulin signal transduction pathway has now been established. In one instance, Rat-1 fibroblasts expressing the human insulin receptor (HIRcB cells) were grown in the presence or absence of insulin. Integrins present on HIRcB cells were immunoprecipitated using anti-integrin antibodies, the precipitates were separated on SDS-PAGE, and subsequently blotted with antiphosphotyrosine antibodies. In those cells treated with insulin, immunoprecipitates obtained with $\alpha_v$ and $\beta_3$ integrin subunit antibodies contained a tyrosine phosphorylated 185 kDa band. Cells grown without insulin also exhibited $\alpha_v$ and $\beta_3$, however the 185 kDa band was absent, indicating it had not associated with $\alpha_v\beta_3$ in these cells.

The 185 Kda band is now known to be insulin receptor substrate-1 (IRS-1), which is the major target protein phosphorylated on tyrosine by ligand-activated receptor for insulin and insulin-like growth factor, and which has an apparent molecular mass of 185 Kd on SDS-polyacrylamide gels (Myers and White, *Diabetes* 42:643 (1993); White and Kahn, *J. Biol. Chem.* 269:1 (1994); Keller and Lienhard, *Trends Cell Biol.* 4:115 (1994)). Tyrosine-phosphorylated IRS-1 appears to connect the activation of the insulin receptor to a number of downstream intracellular signaling pathways by binding signaling molecules containing the Src homology 2 (SH2) -domain. Such proteins include the Ras guanine-nucleotide-releasing complex Grb2-Sos, phosphatidyl inositol 3'-kinase (PI 3-kinase), the phosphotyrosine phosphatase Syp, and the adaptor protein Nck (Myers and White, *Diabetes* 42:643 (1993); White and Kahn, *J. Biol. Chem.* 269:1(1994); Keller and Lienhard, *Trends Cell Biol.* 4:115 (1994)).

Further testing was performed on the FG human pancreatic carcinoma cells which express the $\alpha_v\beta_5$ integrin but not the $\alpha_v\beta_3$ integrin and the FG-B subline which expresses both $\alpha_v\beta_5$ and $\alpha_v\beta_3$ integrins. These studies confirmed association of $\alpha_v\beta_3$ specifically, and not $\alpha_v\beta_5$, with the insulin receptor pathway when cells were contacted with a ligand for each receptor.

These experiments demonstrate that insulin stimulation promotes association of the $\alpha_v\beta_3$ integrin with insulin receptor substrate-1 (IRS-1), an intracellular protein that mediates insulin and insulin-like growth factor signaling. Cells expressing the $\alpha_v\beta_3$ integrin, a vitronectin receptor, responded to insulin with greater DNA synthesis when plated on vitronectin than on other substrates, whereas cells expressing another vitronectin receptor, $\alpha_v\beta_5$, did not show this difference. This demonstrates the specificity of the $\alpha_v\beta_3$ integrin-IRS-1 association, as well as suggests a mechanism for synergistic action of the two ligands. Increased DNA synthesis for a cell population is an indication of promotion of cell proliferation.

Figure 5:
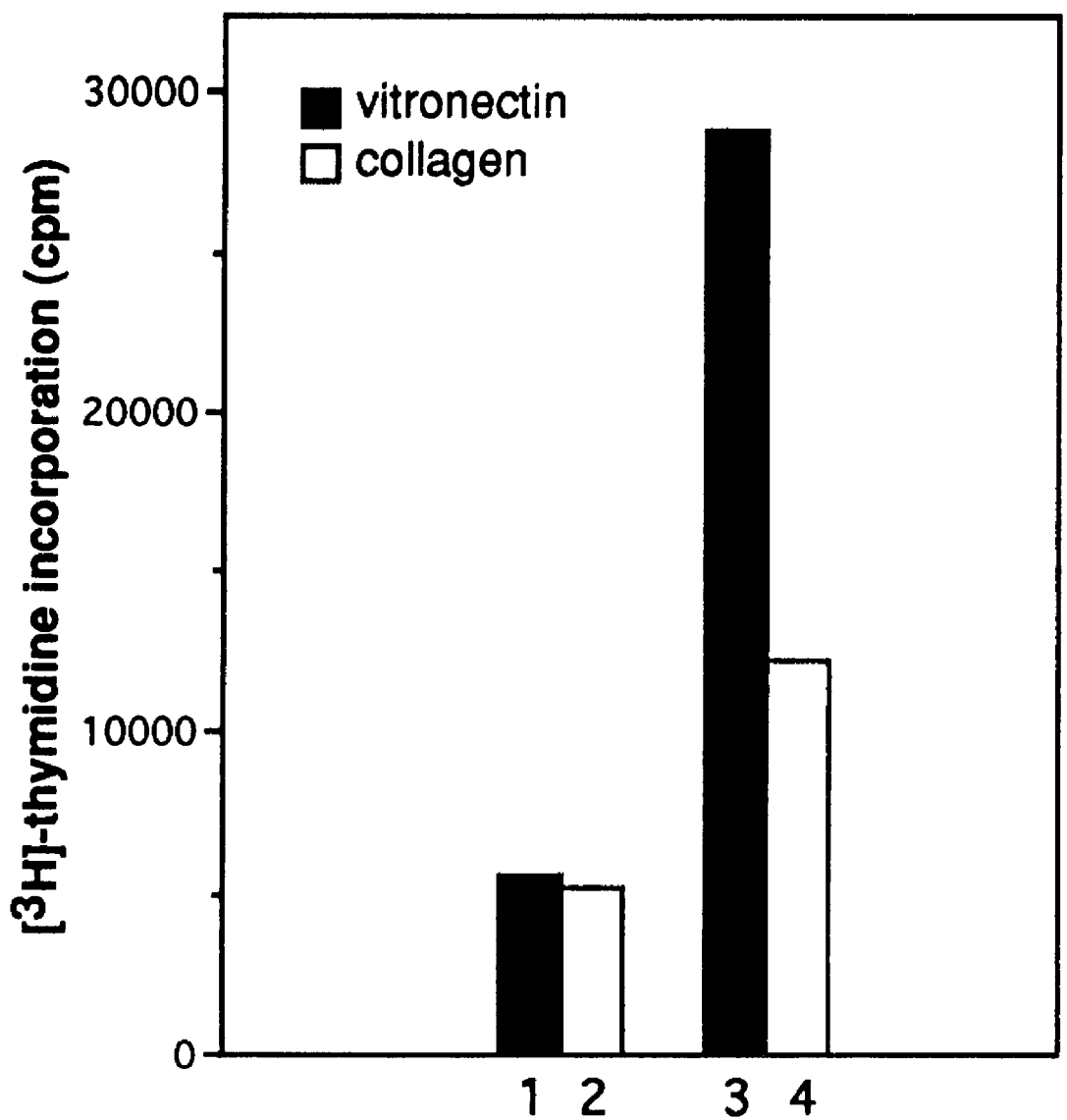
FIG. 5 shows DNA synthesis in human fibroblasts plated on vitronectin or collagen with (columns 3 and 4) and without (columns 1 and 2) PDGF treatment.

Similarly, PDGF promotes DNA synthesis in human fibroblasts when administered in conjunction with the $\alpha_v\beta_3$ ligand vitronectin, as shown in the Example below. When the human fibroblast cells were plated on collagen, which is not a $\alpha_v\beta_3$ ligand, these cells did not show enhanced $^3$H-thymidine incorporation into DNA as can be seen in FIG. 5. In contrast, when Rat-1 cells were plated on vitronectin and treated with EGF, DNA synthesis was not enhanced compared to that exhibited by the same cells treated with EGF and plated on collagen. Thus, the synergistic effect observed for PDGF in conjunction with $\alpha_v\beta_3$ ligand is not present for EGF.

Therefore, these results indicate that some growth factor receptor ligands, but not others, together with $\alpha_v\beta_3$ integrin-mediated cell adhesion promote cell proliferation in a synergistic manner which exceeds that achieved by either the growth factors or $\alpha_v\beta_3$-mediated cell adhesion individually.

Based on this finding, the present invention provides a composition for promoting cell attachment, migration, and proliferation useful in wound healing and tissue regeneration. The composition contains a first ligand to an $\alpha_v$-containing integrin, preferably a ligand to $\alpha_v\beta_3$, and a second ligand to a growth factor receptor. The composition also includes a matrix. The matrix serves as a physical support for cell migration and tissue repair, as well as a delivery vehicle for the growth factor. Thus, the composition of the present invention contains a matrix support, a ligand for the $\alpha_v\beta_3$ integrin, and a ligand for a growth factor receptor. In a preferred embodiment, the matrix is a biodegradable polymer capable of forming a conjugate with the integrin ligand and further containing the growth factor dispersed within it. In addition to containing a ligand for the $\alpha_v\beta_3$ integrin, a ligand for a growth factor receptor, and a matrix, the composition of the present invention also may contain one or more ligands for other integrin receptors, and/or additional ligands for growth factor receptors.

INTEGRIN LIGAND

Ligands to $\alpha_v$-containing integrins, in particular the $\alpha_v\beta_3$ integrin, have proven to be effective in producing the desired synergistic activity in combination with a growth factor receptor ligand.

As used herein, the term "ligand for the $\alpha_v\beta_3$ integrin" or "$\alpha_v\beta_3$ integrin ligand" refers to all compounds capable of binding the $\alpha_v\beta_3$ integrin and thereby triggering a desired biological response, such as cell adhesion, cell migration, differentiation, and the like. Whether a compound binds to $\alpha_v\beta_3$ integrin can be readily determined by methods known in the art, such as an $\alpha_v\beta_3$ ELISA, cell binding assays, binding to $\alpha_v\beta_3$ affixed to a column. Such assays are described, for example, in Pytela et al., *Methods Enzymol.* 144:475 (1987), which is herein incorporated by reference. To determine if a compound that binds $\alpha_v\beta_3$ also triggers a biological response, that compound is contacted with a cell expressing $\alpha_v\beta_3$ and the response evaluated. For instance, a compound that binds $\alpha_v\beta_3$ and triggers cell adhesion can be detected by coating a substrate with the compound, contacting a cell expressing $\alpha_v\beta_3$, such as the cells described herein, with the coated substrate, and assaying for cell adhesion to the substrate. Cell migration can also be evaluated by contacting cells with a substrate coated with a potential ligand and evaluating cell motility on the substrate. Such assays are described in the references, for example, Vuori and Ruoslahti, *J. Biol. Chem.* 268:21459 (1993), and Zhang et al., *J. Cell Biol.* 122:235 (1993), both of which are herein incorporated by reference.

$\alpha_v\beta_3$ integrin-binding ligands include Arg-Gly-Asp and D-Arg-Gly-Asp containing peptides having cell attachment promoting activity, as described in U.S. application Ser. No. 08/176,999, now abandoned, and U.S. Pat. No. 5,120,829, both of which are incorporated by reference, which are hereinafter referred to as peptide ligands. Peptide ligands containing the Arg-Gly-Asp and D-Arg-Gly-Asp sequence are capable of promoting cell attachment when they are presented on a matrix or as an insoluble substrate as well as inhibiting cell attachment to vitronectin or other adhesive proteins when in solution. As used herein, the terms "Arg-Gly-Asp" peptide or "RGD peptide" refer to a peptide having at least one Arg-Gly-Asp-containing sequence which can function as a binding site for an integrin type receptor, as described, for example in Ruoslahti et al., *In Morphoregulatory Molecules*, G. M. Edelman et al, ed. (1990) and Ruoslahti et al., *J. Clin. Invest.* 87:1 (1991), both of which are incorporated by reference. It is intended that the term "RGD peptide" in its broadest sense includes a peptide comprising Arg-Gly-Asp or a functional equivalent. For example, an amino acid such as lysine, homoarginine (homoArg) or a mimic of these amino acids is a functional equivalent of arginine. Similarly mimics of Gly and Asp are functional equivalents of glycine and aspartic acid, respectively. Therefore, a peptide including, for example, Lys-Gly-Asp is considered an RGD peptide within the meaning of the present invention. As used herein, the term "mimic" means an amino acid or an amino acid analog that has the same or similar functional characteristic of an amino acid. Thus, for example, an arginine analog can be a mimic of arginine if the analog contains a side chain having a positive charge at physiological pH, as is characteristic of the guanidinium side chain reactive group of arginine. A peptide mimetic or peptidomimetic is an organic molecule that retains similar peptide chain pharmacophore groups as are present in the corresponding peptide. Peptide mimetics also can be functional equivalents of Arg-Gly-Asp.

As used herein, the term "amino acid" in its broadest sense includes naturally occurring proteogenic amino acids and imino acids as well as non-naturally occurring amino acids and imino acids and analogs and mimics thereof. As used herein, the term "proteogenic" indicates that the amino acid can be incorporated into a protein in a cell through well-known metabolic pathways. In view of this broad definition of an amino acid, one of skill in the art would know that this definition includes, unless otherwise specifically indicated, naturally occurring proteogenic (L) amino acids, (D) amino acids, chemically modified amino acids including amino acid analogs, naturally occurring non-proteogenic amino acids such as norleucine and chemically synthesized compounds that have properties known in the art to be characteristic of an amino acid.

A preferred $\alpha_v\beta_3$ integrin ligand of the present invention is G(dR) (dR) (dR) (dR) (dR) GGG(dR)GDSPASSK (Seq ID No. 1), also known as WH-18. dR refers to the D isomer of arginine; all other amino acids are identified using the common one letter code. The peptide-ligands including WH-18 can be produced synthetically or recombinantly or derived from naturally occurring ligands such as fibronectin or vitronectin.

Peptide ligands are synthetic and relatively easy to manufacture and do not need to be extracted from blood. In addition, the smaller size of the peptides allows many more binding sites to be attached to a given volume of matrix-like polymer. These peptides are also much more stable than fibronectin or other larger molecules in solution. In particular, D-Arg confers protease resistance. Moreover, because they do not carry species-specific immunological determinants, they can therefore be used in both veterinary and human applications. Preferably such peptides contain at least one group of at least three amino acids selected from the D or L forms of Arg, Lys, or ornithine to the N terminal side of the Arg-Gly-Asp sequence.

$\alpha_v\beta_3$ integrin ligands also include larger extracellular matrix proteins such as vitronectin or biologically active fragments thereof. These ligands are combined with the growth factor receptor ligands and preferably attached to a polymer to form a matrix which is applied to wounds. $\alpha_v\beta_3$ integrin ligands also include all synthetic, non-peptide compounds capable of binding the $\alpha_v\beta_3$ integrin, and producing the desired biological response.

The $\alpha_v\beta_3$ integrin is involved in a variety of cellular activities, including angiogenesis, tumor cell migration, and bone resorption. The $\alpha_v\beta_3$ integrin is also known to be present in fibroblasts and migrating epidermal keratinocytes. Synthetic peptides and other synthetic compounds designed to bind $\alpha_v\beta_3$ and thereby modulate its activity in these and other cellular processes are considered $\alpha_v\beta_3$ integrin ligands according to this invention. Thus $\alpha_v\beta_3$ integrin ligands according to EP 578,083 and Koivunen et al., *J. Biol. Chem.* 268:20205 (1993), both of which are incorporated herein by reference, are $\alpha_v\beta_3$ integrin ligands if they are capable of binding $\alpha_v\beta_3$ and triggering a desired biological response.

GROWTH FACTOR LIGAND

The growth factor receptor ligand includes ligands to the insulin receptor, the insulin-like growth factor (IGF) receptor, the platelet derived growth factor (PDGF) receptor, and the interleukin-4 (IL-4) receptor. As used herein the term "ligand" to a growth factor receptor refers to all compounds capable of binding to one of the receptors listed above, and thereby activating cells containing the receptor. Binding is determined using well known receptor-ligand binding techniques. Activation is evidenced by phosphorylation of related internal signal molecules, enhanced DNA synthesis, and other parameters which would be known to those of skill in the art. For example, insulin, IL-4, and insulin-like growth factor bind a receptor and effect phosphorylation of the IRS-1 molecule associated with the insulin receptor (as seen in Example I below, and as described in Sun et al., *Nature* 352:73 (1991), Morla et al., *Mol. Cell. Biol.* 8:2214 (1988)). PDGF binds a receptor and effects the phosphorylation of a 190 kDa protein, as described in Bartfeld et al., *J. Biol. Chem.* 268: 17270 (1993). Compounds which are capable of binding to receptors for PDGF, insulin, insulin-like growth factor, or IL-4 and effecting phosphorylation of IRS-1 or the 190 kDa protein associated with PDGF binding, for example, are considered ligands to a growth factor receptor according to the present invention.

Growth factor receptor ligands include substantially purified growth factors such as all active forms of insulin, insulin-like growth factor (IGF), interleukin-4 (IL-4) and platelet-derived growth factor (PDGF), or biologically active analogs thereof. IGF receptor ligands, insulin receptor ligands, IL-4 receptor ligands, and PDGF receptor ligands may be obtained by synthetic or recombinant production, from commercial sources, or otherwise obtained as would be known by one of skill in the art. For example, U.S. Pat. No. 4,861,747, which is herein incorporated by reference, describes a method for purifying PDGF from human platelets, as well as a method for producing it recombinantly, for example, in mammalian cell cultures infected with Simian Sarcoma virus. Growth factors which are purified from natural sources or recombinantly produced are readily available commercially, for example, from Amgen (Thousand Oaks, Calif.), and Genzyme (Cambridge, Mass.). The B chain of recombinant human BB homodimeric platelet-derived growth factor (rPDGF-BB) is commonly used for clinical purposes. Insulin is readily obtainable from several sources including Sigma (St. Louis, Mo.). IGF and IL-4 are commercially available from several sources, including Genzyme (Cambridge, Mass.).

A concentration of about 0.1 $\mu g/cm^2$ to 10 $\mu g/cm^2$ of relatively pure PDGF, IGF, IL-4 and insulin or analogs thereof produces the desired effect when combined with an effective concentration of $\alpha_v\beta_3$ integrin ligand.

MATRIX

In addition to the ligand components, the compositions of the present invention also include a matrix, which facilitates the administration of the composition to a wound site and provides a provisional scaffold for cell attachment and migration. As used herrin, the term "matrix" refers to a biocompatible solid or non-solid support which functions as a scaffold for tissue repair when $\alpha_v\beta_3$ ligands are attached. The matrix is preferably a biodegradable polymer capable of conjugating to an $\alpha_v$-containing ligand as described in U.S. application Ser. No. 08/176,999, now abandoned, and application number WO 89/05771, which is herein incorporated by reference, as well as containing the growth factor receptor ligand of the composition. Examples of such polymers include hyaluronate, chondroitin sulfate, heparin, heparan sulfate, polylactate, polyglycolic acid, starch or gelatin.

These biodegradable polymers are preferably provided as a conjugate together with a ligand to the $\alpha_v\beta_3$ integrin to form a "synthetic matrix". A preferred biodegradable polymer component of the compositions of the present invention is hyaluronic acid (HA). Hyaluronic acid consists of alternating residues of D-glucuronic acid and N-acetyl-D-glucosamine. The polymer is naturally found in the dermal matrix and is commercially available from many sources in pure form. It can form gels or viscous solutions because it is a water soluble polymer. Other gel forming biodegradable polymers that can be advantageously used include, but are not limited to, collagen, agarose and starch. The polymers may be cross-linked to stabilize their physical properties.

An alternatively preferred biodegradable polymer particularly for ophthalmic applications, is chondroitin sulfate, due to its ability to specifically bind exposed collagen/matrix. Such conjugates form stable solutions which can be provided in liquid form, such as eye drops. Other polymers that can be advantageously used include heparin, heparan sulfate, dextran, polylactate and polyglycolic acid. In addition, these materials could be used in dermal application by crosslinking them to form a gel, or by forming mesh-like structures. The preparation of a peptide-chondroitin sulfate ionic conjugate held together by the ionic interaction between peptide and chondroitin sulfate is described in Japanese patent application number 3-220614 (publication number 6-80694), which is herein incorporated by reference.

Effective concentrations of the $\alpha_v\beta_3$ integrin ligand and the growth factor receptor ligand in the matrix for a particular purpose may be determined using assays and techniques well known in the art. The optimum concentration of each ligand within a matrix is determined independently. For example, a variety of matrices can be assembled, each containing a different ratio of the $\alpha_v\beta_3$ integrin ligand to matrix weight, for example, combinations of 40% to 100% ligand to matrix by weight. Each combination is then evaluated for its ability to support cell attachment and migration using in vitro and in vivo assays as described in the examples below. The combination supporting the greatest amount of cell adhesion and migration is then combined with a range of concentrations of growth factor receptor ligand and tested for the ability to promote cell proliferation in addition to supporting cell attachment and migration. Cell proliferation can be measured using thymidine incorporation, as described in Example III below, as well as cell counting techniques well known in the art. An effective ratio of ligands within a matrix is that which supports cell proliferation, cell attachment and cell migration.

The $\alpha_v\beta_3$ integrin ligand and matrix components of the conjugate can be joined by a number of procedures. They are joined using 1-ethyl-3-3-dimethylaminopropylcarbodmiide (EDC), a cross-linking/coupling agent. Other cross-linking/coupling reagents can also be used such as dicyclohexylcarbomide (DDC), glutaraldehyde, cyanogen bromide or N-hydroxysuccinimide. Other methods, well known in the art, can alternatively be used.

Growth factor receptor ligands such as active forms of PDGF are incorporated into the synthetic matrix conjugate in order to produce the composition of the present invention. The ratio of ligands to polymer scaffold will vary depending on the intended usage and can be determined by the methods and assays disclosed herein. These ligands can be advantageously incorporated into a synthetic matrix described above using cross-linking. The growth factor receptor ligand can be added to the hyaluronic acid scaffold, for example, using epoxides such as butane 1,4-butanediol diglycidyl epoxide (BDDE), polyglycerolpolyglycidyl ether (PGPGE), according to a method similar to that described in Yui et al. *J. Controlled Rel.* 24:133 (1993), which is herein incorporated by reference. The use of epoxide for the immobilization of growth factor receptor ligands allows for the potential of controlled release from the matrix because ester bonds formed at low pH are hydrolyzable. This methodology will not affect the activities of peptide ligands since the primary amine of the peptides do not react with the epoxide at low pHs.

Alternatively, growth factor receptor ligands can be incorporated into peptide ligand/polymer matrices using entrapment within microspheres in a method similar to that described in Goa et al. *Drugs* 47:536 (1993), which is herein incorporated by reference, or hyaluronic acid ester microspheres. Entrapment consists of modifying the hyaluronic acid chain/peptide integrin conjugate to contain a surplus of positive charges when in place on the matrix. For example, a preferred peptide G(dR) (dR) (dR) (dR) (dR)GGG(dR) GDSPASSK (Seq ID No. 1) contains six argidines and has a net of six positive charges. Another method to entrap proteins is the use of photoactivation methods to induce free radical polymerization, according to Pathak et al. *J. Am Chem Soc* 114:8311 (1992), which is herein incorporated by reference, using in this case a photoactive dye such as eosin Y.

Alternatively, in some cases, the growth factor receptor ligands can be cross-linked to form a co-polymer which could be cross-linked to the synthetic matrix described above. The growth factor receptor ligands could also be mixed into the $\alpha_v\beta_3$ ligand matrix and thereby incorporated into the composition.

The use of HA and other biodegradable polymer scaffolds containing bioactive components advantageously provides a matrix which stabilizes the bioactive components and provides a provisional matrix for cell migration and tissue repair. This is particularly important when growth factors or analogs are the growth factor receptor ligands, since many growth factors have been found to break down before a therapeutic effect can be produced.

Release of the growth factor receptor ligand from the synthetic matrix such as hyaluronic acid can be assured by the subsequent application of hyaluronidase, for example. However, it has been found that the matrix breaks down over time when applied to a wound to provide a steady release of the bioactive components (see, for example, Polarek et al., *Wounds* 6 (2):46 (1994) at page 50, which is herein incorporated by reference) since the biodegradable polymer scaffolds are selected so as to be normally broken down when applied to a skin surface.

The viscosity of the semi-gel can be altered by the addition of unconjugated hyaluronate or varying the degree of peptide conjugate. The semi-gel can be placed directly in a wound to aid in healing by providing an artificial biodegradable matrix along with cell attachment, migration, and proliferation signals. In alternate embodiments the conjugate can be coated on a biodegradable mesh or other implanted material, or it can itself be formed into sheets or other structures, or can be provided as a stable solution.

As a semi-gel, the conjugate does not tend to migrate away from the wound site, either due to physical effects such as movement by the patient or by absorption by the patient's own system. The conjugate acts as a temporary replacement matrix that encourages cell migration into the wound and speeds healing. As the wound heals, the conjugate is slowly broken down by the migrating cells and replaced by natural replacement matrix. For other applications, such as with corneal abrasion caused by the dry eye condition or other circumstances, a conjugate consisting of an $\alpha_v\beta_3$ receptor ligand coupled to chondroitin sulfate and having a growth factor is preferable. This conjugate binds to expose dermis collagen matrix, proving attachment sites for corneal epithelial cells. Such material can be provided in liquid form, such as eye drops.

Various compositions in the form of hyaluronic acid scaffolds (HA scaffolds) containing varying proportions of the two ligands can be tested in commonly used in vivo dermal wound healing models such as those described for the RGD polymer conjugates described in U.S. patent application Ser. No. 08/176,999, now abandoned. Such compositions can be used on any wounds which involve body tissues being cut, abraded or otherwise damaged. Such wounds include chronic skin ulcers, burns, corneal wounds and incisions. Regeneration of tissue (such as cartilage, bone, or nervous tissue) can also be enhanced by applying the compositions of the present invention. Additional in vivo animal models useful for testing compositions of the present invention include subcutaneous implantation of the composition in guinea pigs (Polarek et al., supra (1994), Buckley et al., *PNAS USA* 82: 7340 (1985)); rat incisional models (Shah et al., *Lancet,* 339: 213 (1992); rabbit ear ulcer model (Pierce et al., *Amer. J. Path.,* 138: 629–646 (1991); rabbit knee femoral medial condyl defect (Von Shroeder et al., *J. Biomed. Mater. Res.* 25:329 (1991); and pig burn model (Polarek et al., supra (1994)), all of which are herein incorporated by reference. Those of skill understand that the results of such in vivo experiments are analyzed for enhanced tissue deposition, rate of epithelialization, cell type reactivity, and growth factor delivery.

The compositions of the present invention are therefore preferably provided in the form of synthetic matrices with the two types of ligand incorporated as described above. Compositions in the form of matrices or semi-gels are easily applied to wound areas as described above and in U.S. patent application Ser. No. 08/176,999, now abandoned. For example, a semi-gel can be applied to dermal wounds such as chronic ulcer wounds resulting from various disease conditions such as diabetes or sickle-cell anemia which result in slower than normal wound healing. The semi-gel containing the two types of ligands is applied topically to the wound, and the ulcer covered with a gauze dressing. Clinical studies employing a conjugate of HA and WH-18, the preferred $\alpha_v\beta_3$ integrin ligand (known as ARGIDENE™ gel or Telio-Derm®, Telios Pharmaceuticals, San Diego, Calif.) are described in Wethers et al. *Blood* 84:1775 (1994), which is herein incorporated by reference. In addition, the peptides described in U.S. Pat. No. 5,120,829, which is herein incorporated by reference, can also be used as ligands.

The present invention also provides a method of promoting wound healing by applying the composition of the present invention. A preferred form of the composition for use in this method is a composition which includes a ligand for the PDGF receptor. For example, a preferred embodiment of a composition for promoting wound healing is a synthetic hyaluronic acid matrix containing the WH-18 peptide and a ligand for the PDGF receptor, such as PDGF. The method of applying the composition contemplated by the present invention is identical to the methods disclosed for the synthetic matrix lacking the growth factor ligand with the exception of instances where an additional enzyme is applied over the semi-gel to hasten the synthetic matrix breakdown.

In addition, a method of promoting tissue regeneration is provided by the present invention by applying the compositions of the present invention in a manner described above.

The compositions of the present invention are also useful as matrices to support cell growth and tissue regeneration in vitro. The ligand-containing matrix can be used to coat surfaces to support and enhance primary and secondary tissue cultures, for example.

The following examples are intended to more clearly illustrate aspects of the invention, but are not intended to limit the scope thereof.

EXAMPLES

Throughout these examples, various publications are referred to more fully disclose the state of the art. These references are hereby incorporated by reference.

EXAMPLE I

Association of p185/IRS-1 with Integrins

The following studies demonstrate that the $\alpha_v\beta_3$ integrin, but not the $\beta_1$ integrins or the $\alpha_v\beta_5$ integrins, is associated with a known signal transduction protein, the insulin receptor substrate 1 (IRS-1) protein, also known as 4PS. The cDNA for IRS-1 encodes a cytoplasmic protein with a calculated molecular weight of 131 kDa, however IRS-1 migrates at 165–185 kDa on SDS-PAGE (Sun et al., *Nature* 352:73 (1991), White and Kahn, *J. Biol. Chem.* 269:1 (1994)). IRS-1 is constitutively phosphorylated on serine and threonine residues and becomes heavily phosphorylated on tyrosine after insulin stimulation. IRS-1 has no known enzymatic function, but is capable of binding a number of proteins that recognize its phosphorylated tyrosine residues through their SH2 (src homology 2) domains. Such proteins include phosphatidyl inositol-3-kinase (PI-3 kinase) and the adaptor protein Grb2. One known consequence of these interactions is the enhancement of PI-3 kinase activity. Thus IRS-1 is thought to mediate the actions of insulin receptor by connecting the receptor to a number of signaling pathways. IRS-1 is also phosphorylated by the insulin-like growth factor (IGF-1) (Sun et al., supra (1991)), and following stimulation of cells with IL-4 (Morla et al., *Mol. Cell Biol.* 8:2214 (1988), *Proc Natl Acad Sci USA* 90:4032 (1993)).

Integrins were immunoprecipitated from Rat-1 fibroblasts (HIRcB cells) that had been stably transfected with the human insulin receptor, as described in McClain et al., *J. Biol. Chem.* 262:14663 (1987). HIRcB cells used in these experiments were obtained from Dr. Jerrold M. Olefsky, University of California, San Diego, Calif. Immunoblotting with anti-phosphotyrosine antibodies was performed to determine whether tyrosine-phosphorylated proteins were coprecipitated. Two polyclonal antisera raised against human placental vitronectin receptor (anti-$\alpha_v\beta_3$ antibodies) and a polyclonal antibody raised against the platelet $\alpha_{IIb}\beta_3$ integrin coprecipitated a 185-kD phosphorylated protein (p185) from insulin-stimulated HIRcB cells as shown in FIG. 1A, lanes 3, 4, 5.

FIG. 1A shows cell lysates from quiescent (lane 1) or insulin-stimulated (lanes 2 to 8) HIRcB cells. HIRcB cells were grown to 80% confluency in Dulbeccos's modified Eagle's medium (DMEM) containing 10% fetal calf serum (FCS) and 500 nM methotrexate, incubated in DMEM+ 0.1% BSA for 36 hours, and either left quiescent, or stimulated with 100 nM insulin (Sigma) for 3 minutes. Cell monolayers were rinsed with PBS, frozen with liquid nitrogen and lysed in NP-40 lysis buffer (20 mM Tris-HCl (pH 8.0), 1% NP-40, 10% glycerol, 137 mM NaCl, 1 mM CaCl$_2$, 1 mM MgCl$_2$, 1 mM sodium orthovanadate, 50 mM sodium fluoride, 1 mM phenylmethylsulfonylfluoride, 0.1 U/ml aprotinin, 10 $\mu$g/ml pepstatin A). HIRcB cells were immunoprecipitated with anti-$\alpha_v\beta_3$ 237 according to Suzuki et al., *PNAS* USA 83:8614 (1986), as shown in lanes 1 and 3, 237 preimmune serum in lane 2, anti-$\alpha_v\beta_3$ 1343 in lane 4, anti-$\alpha_{IIb}\beta_3$ in lane 5, anti-$\alpha_5\beta_1$ 488 in lane 6 (made according to Argraves et al., *J. Cell Biol.* 105:1183 (1987)) and an unrelated rabbit antiserum (lane 7). Anti-$\alpha_v\beta_3$ 1343 was obtained from Ms. Helena Hessle (Telios Pharmaceuticals, Inc.) and anti-$\alpha_{IIb}\beta_3$ from Dr. Elisabetta Dejana (Mario Negri Institute, Milan, Italy). Three anti-$\alpha_5\beta_1$ antibodies and six unrelated polyclonal antibodies tested gave results similar to those shown in lanes 6 and 7. Separate stained gels showed that each of the integrin antibodies immunoprecipitated the appropriate integrins (not shown). In lane 8, anti-$\alpha_v\beta_3$ 237 immunocomplexes from insulin-treated cells were dissociated and reprecipitated with the same antibody as follows. Anti-$\alpha_v\beta_3$ 237 immunocomplexes from insulin-treated cells were resuspended in 10 mM Tris-HCl (pH 7.5), 2% SDS, 1 mM sodium orthovanadate, 50 mM sodium fluoride, and heated at 95 degrees C. for 5 minutes. The supernatant was diluted 10-fold to 10 mM Tris-HCl (pH 7.5) and reprecipitated with the anti-$\alpha_v\beta_3$ 237 antibody. Similar results were obtained with anti-$\alpha_v\beta_3$ 1343 and anti-$\alpha_{IIb}\beta_3$ antibodies.

The immunocomplexes were analyzed by SDS-polyacrylamide gel electrophoresis (SDS-PAGE) and immunoblotted with a monoclonal anti-phosphotyrosine antibody and $^{125}$I-labeled anti-mouse IgG. Anti-phosphotyrosine antibody py20, anti-Grb2 mAb and polyclonal antibody against the 85-kD subunit of PI 3-kinase were obtained from Transduction Laboratories (Lexington, Ky.). $^{125}$I-labeled anti-mouse IgG was obtained from Amersham Corp, Arlington Heights, Ill.

No phosphorylated protein was precipitated if the HIRcB cells were not insulin-stimulated (see FIG. 1A, lane 1). No coprecipitation of p185 occurred when polyclonal antibodies against the $\alpha_5\beta_1$ integrin were used (FIG. 1A, lane 6). The Rat-1 (HIRcB) cells express this fibronectin receptor; however, as all $\beta_1$ integrins are precipitated by this antibody, the result demonstrates that the other $\beta_1$ integrins fail to associate with p185 as well. Cell surface iodination followed by immunoprecipitation with antibodies against integrin subunit cytoplasmic domains showed that at least the $\alpha_3\beta_1$ and $\alpha_5\beta_1$ integrins are expressed by the HIRcB cells. Both of these β1-integrins were expressed at approximately the same level as $\alpha_v\beta_3$. Antibodies against several unrelated proteins also failed to coprecipitate p185 (FIG. 1A, lane 7). When anti-$\alpha_v\beta_3$ immunocomplexes were dissociated in SDS and reprecipitated with the same antibodies, p185 was not detectable in the reprecipitated receptor complex. Immunoblot analysis with anti-$\alpha_v\beta_3$ antibodies showed that the $\alpha_v\beta_3$ integrin is precipitated with anti-$\alpha_v\beta_3$ antibodies to the same extent with and without SDS treatment. This has also been demonstrated for the anti $\alpha_v\beta_3$ 237, as described in Bartfeld et al. *J. Biol. Chem.*268:17270 (1993). The anti-integrin antibodies therefore do not directly cross-react with p185 under these conditions (FIG. 1A, lane 8).

Moreover, human cells were tested with commonly available monoclonal antibodies (mAbs); two mAbs reactive with the $\alpha_v$-integrins coprecipitated p185, an anti-$\beta_1$ and an anti-$\alpha_5$ mAb did not (data not shown).

Isolation of HIRcB cell integrins on an RGD-peptide column confirmed the association of p185 with integrins. The phosphorylated p185 copurified with detergent extracts from insulin-treated cells on GRGDSPK (Seq ID NO. 2) -Sepharose, a known ligand for $\alpha_v\beta_3$ and other integrins (Ruoslahti and Pierschbacher, *Cell* 44:517 (1986); Ruoslahti and Pierschbacher, *Science* 238:491 (1987)), but not on a control peptide linked to Sepharose (FIG. 1B, lanes 1 and 2).

FIG. 1B shows cell lysates from insulin-stimulated HIRcB cells. After insulin stimulation, 5×10⁸ HIRcB cells were lysed in octylglucoside buffer [100 mM octyl-β-D-glucopyranoside in PBS containing 1 mM $CaCl_2$, 1 mM $MgCl_2$], and the following phosphatase and protease inhibitors: 1 mM sodium orthovanadate, 50 mm sodium fluoride, 1 mM phenylmethylsulfonylfluoride, 0.1 U/ml aprotinin, 10 μg/ml leupeptin and 4 μg/ml pepstatin A. Octylglucoside was used as the detergent in affinity chromatography, because it is known to give a higher yield of integrins than other detergents (Pytela et al., *Methods Enzymol.* 144:475 (1987)). Integrins were isolated on GRGDSPK (Seq. D No. 2) -Sepharose (lane 1) or GRGESPK (Seq. ID No. 3)-Sepharose (lane 2) as described in Pytela et al., supra, and eluates were analyzed by anti-phosphotyrosine immunoblotting.

It is known that the insulin receptor substrate 1 (IRS-1) is the major target protein phosphorylated on tyrosine by ligand-activated insulin receptor and has an apparent molecular mass of 185 kD on SDS-polyacrylamide gels (Myers and White, *Diabetes* 42:643 (1993); White and Kahn, *J. Biol. Chem.* 269:1(1994); Keller and Lienhard, *Trends Cell Biol.* 4:115 (1994)). Immunoblot analysis with an antiserum against the $NH_2$-terminus of IRS-1 is shown in FIG. 1C. The anti-IRS-1 antibody prepared against the $NH_2$-terminus of IRS-1 (as described in Rose et al., *PNAS USA* 91:797 (1994) and provided by Dr. J. M. Olefsky, UCSD, Calif.), demonstrated the presence of a reactive band in anti-$\alpha_v\beta_3$ immunocomplexes from insulin-stimulated, but not from unstimulated, HIRcB cells.

FIG. 1C shows extracts from quiescent (lanes 1, 3, 5 and 7) or insulin-stimulated (lanes 2, 4, 6 and 8) HIRcB cells immunoprecipitated with anti-$\alpha_v\beta_3$ 237 (lanes 1 and 2), anti $\alpha_v\beta_3$ 1343 (lanes 3 and 4), anti-$\alpha_5\beta_1$ 488 (lanes 5 and 6) and an anti-IRS-1 antibody (lanes 7 and 8). The immunoprecipitates were separated by SDS-PAGE, and immunoblotted with the anti-IRS-1 antibody followed by chemiluminescence detection with anti-rabbit IgG (ECL, Amersham, Arlington Heights, Ill.). The amount of protein loaded in lanes 1 to 6 was five times that in lanes 7 and 8.

Similar results were obtained with two other polyclonal antibodies to IRS-1, one raised against the COOH-terminus of IRS-1, and the other against recombinant IRS-1 produced in insect cells. Polyclonal anti-IRS-1 antibodies were obtained from Upstate Biotechnology, Inc., Lake Placid, N.Y. Immunoblot analyses were performed as in FIG. 1C. Additionally, dissociation of the anti-$\alpha_v\beta_3$ immunocomplexes from insulin-treated cells followed by reprecipitation with anti-IRS-1 antibodies yielded a band corresponding to IRS-1 as shown in FIG. 1D.

FIG. 1D shows anti-$\alpha_v\beta_3$ 237 immunocomplexes from insulin-treated cells (lane 1) dissociated as in FIG. 1A. The supernatant was subjected to three rounds of reprecipitation with the anti-IRS-1 antibody (lane 2), and the supernatant cleared of IRS-1 was immunoprecipitated with py20 (lane 3) The immunoprecipitates were run on SDS-PAGE and immunoblotted with anti-phosphotyrosine antibodies.

The fact that the bands in FIG. 1D, lanes 1 and 2 were about equal intensity, and the failure of the phosphotyrosine antibody to immunoprecipitate any phosphotyrosine-containing proteins from the dissociated anti-$\alpha_v\beta_3$ complexes after they had been depleted of IRS-1 (FIG. 1D, lane 3), showed that IRS-1 represents a major portion of p185 associated with the vitronectin receptor. Insulin receptor was not detectable in the integrin immunocomplex. Polyclonal anti-insulin receptor antibody was obtained from Upstate Biotechnology, Inc., Lake Placid, N.Y. Immunoblot analyses were performed as in FIG. 1C.

Five to eight percent of IRS-1 was complexed with the vitronectin receptor and maximal association was reached after 3 minutes of insulin stimulation. Comparison of the amount of integrin-associated IRS-1 with the amount of IRS-1 from total cell lysate was carried out by immunoblot analysis as described above for FIG. 1 by using anti-IRS-1 antibody and $^{125}$I-labeled anti-rabbit IgG (Amersham Corp., Arlington Heights, Ill.). Ambis radioanalytic imaging system was used for densitometric analysis of the bands (not shown).

The $\alpha_v\beta_3$-IRS-1 association was also found in normal kidney cells stimulated with IGF-1 (not shown). By using similar immunoprecipitation and immunoblotting techniques, it can be demonstrated that treatment of normal kidney cells with IGF-1, which also signals through IRS-1, would result in the $\alpha_v\beta_3$ -IRS-1 association.

EXAMPLE II

Association of Grb2 and PI 3-Kinase with IRS-1

Immunoblot analysis with anti-Grb2 and anti-PI 3-kinase antibodies showed that both of these proteins coprecipitated with $\alpha_v\beta_3$ integrin when immunoprecipitated with anti-$\alpha_v\beta_3$ antibodies from the insulin-stimulated HIRcB cells (FIG. 2). Both proteins also precipitated with IRS-1 when immunoprecipitated with anti-IRS-1 anitibodies from insulin-stimulated cells.

Figure 2B:
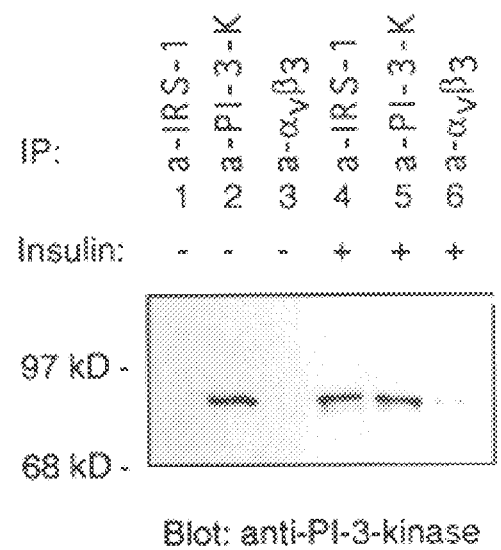
FIG. 2B shows quiescent and insulin-stimulated HIRcB cells immunoprecipitated with various antibodies and immunoblotted with anti-PI 3-kinase antibody.

FIG. 2A shows the association of Grb2 and FIG. 2B shows the association of PI 3-kinase with integrins. Cell lysates from quiescent (lanes 1 to 3) or insulin-stimulated (lanes 4 to 6) HIRcB cells were prepared as described for FIG. 1, and immunoprecipitated with the antibodies indicated. Anti-phosphotyrosine antibody py20, anti-Grb2 mAb and polyclonal antibody against the 85-kD subunit of PI 3-kinase were obtained from Transduction Laboratories (Lexington, Ky.). $^{125}$I-labeled anti-mouse IgG was obtained from Amersham. The amount of protein loaded in (A) in the anti-$\alpha_v\beta_3$ 237 lanes was five times that in the anti-IRS-1 lanes, and ten times that in the anti-Grb2 lanes. In (B), equal amounts of proteins were loaded in the lanes. The immunoprecipitates were separated on SDS-PAGE and immunoblotted with the anti-Grb2 mAb or anti-PI 3-kinase followed by detection with anti-mouse IgG or anti-rabbit IgG, respectively, and chemiluminescence.

EXAMPLE III

Effect of Insulin Stimulation on Human Pancreatic Carcinoma Cells

FG human pancreatic carcinoma cells do not express the $\alpha_v\beta_3$ integrin but rather use integrin $\alpha_v\beta_5$ as their vitronectin receptor as described in Cheresh et al., Cell 57:59 (1989). FG-C is a FG subline transfected with the expression vector pcDNAINeo which does not express $\alpha_v\beta_3$ intregin. FG-B cell line obtained from Dr. D. Cheresh is a FG subline transfected with a full-length $\beta_3$ cDNA in pcDNAINeo, and thus expresses $\alpha_v\beta_3$ as described in Leavesley et al., J. Cell. Biol. 117:1101 (1992). Therefore, as demonstrated by Leavesley et al., the FG-C cells express the $\alpha_v\beta_5$ integrin and $\beta_1$ integrins; the FG-B cells express the $\alpha_v\beta_3$ integrin as well. The expression level of $\beta_1$ in the FG-B cells is about 60% of the expression level of $\beta_1$.

Figure 3:
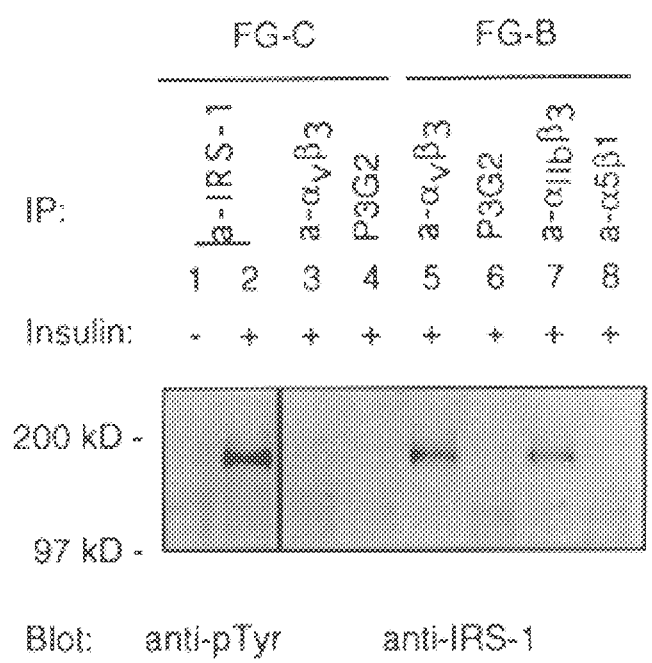
FIG. 3 shows cell lysates of quiescent and insulin-stimulated FG-C ($\alpha_v\beta_3$ integrin negative), and FG-B ($\alpha_v\beta_3$ integrin positive) cells immunoprecipitated with various antibodies, and immunoblotted with antiphosphotyrosine and anti-IRS-1 antibodies.

FIG. 3 shows integrin-IRS-1 association in insulin-stimulated human pancreatic carcinoma cells. IRS-1 becomes tyrosine-phosphorylated in insulin-stimulated FG-C cells (FIG. 3A, lane 2), but it did not associate with the $\alpha_v\beta_5$ integrin (FIG. 3A, lanes 3 and 4). Cell lysates from quiescent (lane 1) or insulin-stimulated (lanes 2 to 7) FG-C cells (lanes 1 to 4) and FG-B cells (lanes 5 to 7) were immunoprecipitated with various antibodies. Immunoprecipitates with anti-IRS-1 antibody are shown in lanes 1 and 2, anti-$\alpha_v\beta_3$ 237 is shown in lanes 3 and 5, mAb P3G2 ($\alpha_v\beta_5$) is shown in lanes 4 and 6, anti-$\alpha_{IIb}\beta_3$ is shown in lane 7, and anti-$\alpha_5\beta_1$ 488 is shown in lane 8. MAb P3G2 against human $\alpha_v\beta_5$ integrin is described in Wayner et al., J. Cell Biol. 113:919 (1991), and was obtained from Dr. D. Cheresh.

Immunoprecipitates of the $\alpha_v\beta_5$ and $\beta_2$-expressing FG-C cells were subjected to SDS-PAGE and immunoblotted with anti-phosphotyrosine (lanes 1 and 2) and anti-IRS-1 (lanes 3 and 4). Anti-IRS-1 precipitated a phosphorylated IRS-1 band from cells treated with insulin, but not from cells grown without insulin. Anti-vitronectin receptor antibodies, however, fail to coprecipitate the IRS-1 band in these cells regardless of insulin treatment (FIG. 3, lanes 3 and 4). As determined by immunoblotting, these antibodies coprecipitate efficiently the $\alpha_v\beta_5$ integrin. This is confirmed by the results in Leavesley, et al., supra and Bartfeld et al., J. Biol. Chem. 268:17270 (1993), showing that the $\alpha_v\beta_5$ integrin does not interact with IRS-1. These findings confirm the absence of $\alpha_v\beta_3$ integrin on FG-C cells, and indicate IRS-1 does not associate with $\alpha_v\beta_5$ in the presence of insulin. In contrast, anti-$\alpha_v\beta_3$ and anti-$\alpha_{IIb}\beta_3$ antibodies (FIG. 3, lanes 5 and 7) coprecipitated IRS-1 from insulin-stimulated FG-B cells that had been stably transfected with a cDNA encoding the integrin $\beta_3$ subunit and thus express the $\alpha_v\beta_3$ integrin. Immunoprecipitation of the $\alpha_v\beta_5$ or $\beta_1$-integrins with anti-$\alpha_v\beta_5$ or anti-$\alpha_5\beta_1$ antibodies, respectively, showed no association of the $\alpha_v\beta_5$ or $\beta_1$-integrins with IRS-1 (FIG. 3, lanes 6 and 8).

In a separate experiment, attachment assays performed according to Pytela et al., PNAS USA 82:5766 (1985), revealed no differences between the adhesion of the FG-B and FG-C cells. Adhesion to vitronectin was inhibited by polyclonal anti-$\alpha_v\beta_3$, but not anti-$\alpha_5\beta_1$, antibodies. The reverse was true for adhesion to collagen; the dependence of collagen adhesion on $\beta_1$-containing integrins has also been demonstrated by inhibition with anti-$\beta_1$ mAb in Cheresh et al., 1989 supra. Therefore, FG-B/FG-C cell adhesion to vitronectin is mediated by $\alpha_v$-integrins, whereas adhesion to collagen is mediated by $\beta_1$-integrins.

Figure 4:
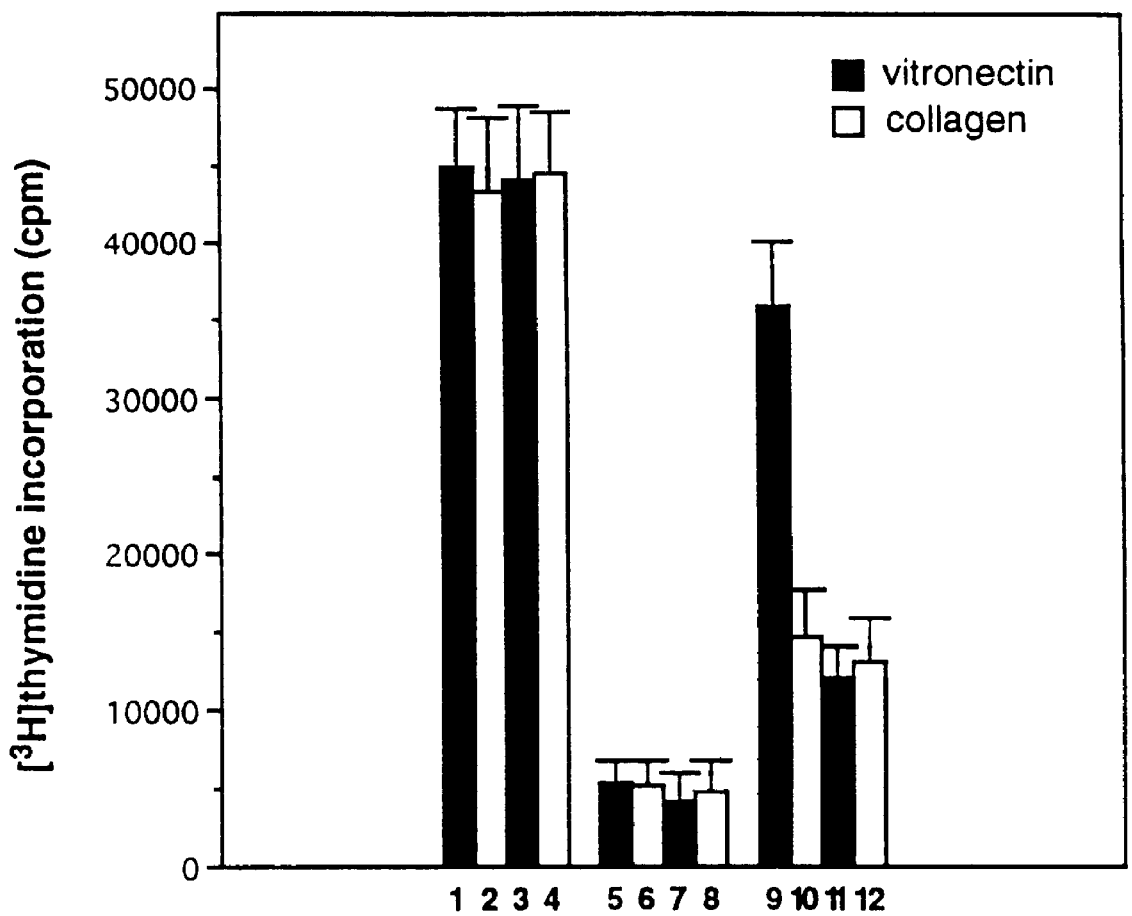
FIG. 4 shows DNA synthesis, as measured by thymidine incorporation, of FG-B ($\alpha_v\beta_3$ integrin positive) and FG-C ($\alpha_v\beta_3$ integrin negative) cells plated on vitronectin or collagen with (columns 9 to 12) and without (columns 1 to 8) insulin stimulation.

FIG. 4 shows DNA synthesis ([$^3$H]-thymidine incorporation into DNA) in insulin-stimulated human pancreatic carcinoma cells on various substrates. FG-B (columns 1, 2, 5, 6, 9, and 10) and FG-C cells (columns 3, 4, 7, 8, 11, and 12) were plated at 1×10$^5$ cells/well on 24-well plates that had been coated either with vitronectin (dark column) or type I collagen (open column) . Plates were coated with 10 $\mu$g/ml of either vitronectin or type I collagen for 12 hours followed by blocking with 0.5% bovine serum albumin For 2 hours. Cells were incubated for 36 hours in DMEM containing 10% FCS (columns 1 to 4), or in DMEM containing 0.1% BSA followed by addition of buffer (columns 5 to 8) or 100 mM insulin (columns 9 to 12). FCS is used as a control because it provides maximal stimulation owing to the presence of high levels of growth factors and adhesion proteins.

Trypan blue exclusion demonstrated cell viability to be over 85% on both vitronectin and collagen after 36 hour incubation in DMEM+0.1% BSA. After 15 hours, the cells were pulse-labeled with 1 $\mu$Ci/ml [$^3$H]-thymidine (specific activity 6.7 Ci/mmol, DuPont NEN) for 3 hours and thymidine incorporation into DNA was determined by trichloroacetic acid precipitation and liquid scintillation counting. Error bars indicate the standard error of triplicate determinations.

The FG-B cells responded to insulin with about 2.5-fold higher DNA synthesis when plated on the $\alpha_v\beta_3/\alpha_v\beta_5$ integrin ligand vitronectin than they did on collagen, where attachment is mediated by $\beta_1$-integrins (FIG. 4, columns 9, 10). The FG-C cells, which lack $\alpha_v\beta_3$, showed no difference in the response on vitronectin and collagen (FIG. 4, columns 3, 4, 7, 8, 11, 12).

A correlation between $\alpha_v\beta_3$ expression and increased insulin responsiveness on vitronectin was also found in a panel of three cell lines expressing $\alpha_v\beta_3$ and three lines expressing only $\alpha_v\beta_5$. By using these cell lines, it was demonstrated that attachment to laminin did not increase insulin responsiveness. The $\alpha_v\beta_3$-expressing cell lines were HIRcB, NIH 3T3 and NRK cells, and the cell lines expressing $\alpha_v\beta_5$ but not $\alpha_v\beta_3$ were HT29 colon carcinoma, UCLA-P3 lung adenocarcinoma and Panc-1 pancreatic carcinoma cells. $\alpha_v\beta_3$ was found to associate with IRS-1 in all the $\alpha_v\beta_3$ expressing cell lines following insulin stimulation. All the cell lines attached equally to vitronectin. NRK, HT29, UCLA-P3 and Panc-1 attached also to laminin and collagen, and HIRcB and NIH 3T3 cells attached to laminin. The attachment to laminin and collagen was inhibited by anti-$\beta_1$ antibodies (Vuori and Ruoslahti, unpublished data, and Hayman et al., J. Cell Biol. 100:1948 (1985); Hayashi et al., J. Cell biol. 110:175 (1990); Schreiner et al., Clin. Expl. Metastasis 9:163 (1991); and Cheresh et al., supra).

In a similar manner to insulin treatment it was demonstrated that NRK cells responded to IGF-1 with about 2.3-fold higher DNA synthesis when plated on vitronectin than they did on collagen or laminin (not shown).

In summary, these results demonstrate physical association of an integrin with a known signaling molecule. The coprecipitation experiments inherently cannot distinguish a preexisting protein-protein association from one that occurs after the cells have been extracted. However, the cell proliferation data suggest that the $\alpha_v\beta_3$ integrin, presumably through its interaction with IRS-1, modulates cellular responses to insulin in a ligand-dependent manner. The integrin association increases the level of phosphorylated IRS-1 at the plasma membrane, where some of the targets for the IRS-1-associated signaling molecules are localized. The effects of insulin on pathways such as the one employing Grb2-Sos and, possibly, PI3-kinase are enhanced as a result.

Unlike the activation of focal adhesion kinase, which seems to be mediated by a number of integrins (Schwartz, M. A., *Trends Cell Biol.* 2:304 (1992); Burridge et al., *Curr. Biol.* 2:537 (1992); Sastry and Horwitz, *Curr. Opin. Cell Biol.* 5:819 (1993); Juliano and Haskill, *J. Cell Biol.* 3:577 (1993); Schaller and Parsons, *Trends Cell Biol.* 3:258 (1993)), the association with IRS-1 appears to be limited to the $\alpha_v\beta_3$ integrin. IRS-1 could therefore mediate integrin-specific signals, such as the enhanced growth response to insulin observed.

EXAMPLE IV

Effect of Ligand Binding of the $\alpha_v\beta_1$ Integrin on DNA Synthesis in PDGF-Stimulated Human Foreskin Fibroblasts This example demonstrates the effect of the ligand binding of the $\alpha_v\beta_3$ integrin on platelet derived growth factor (PDGF)-stimulated cell proliferation measured by DNA synthesis in human foreskin fibroblasts.

Human foreskin fibroblasts (Coriell) were plated at $1\times10^5$ cells/well on 24-well plates that had been coated for 12 hours either with 20 µg/ml of vitronectin of 20 µg/ml of type I collagen. Cells were incubated for 36 hours in Dulbecco's modified Eagle's medium containing 0.1% bovine serum albumin followed by addition of buffer or 40 ng/ml PDGF-BB (Boehringer Mannheim). After 15 hours, the cells were pulse-labeled with 1 µCi/ml [$^3$H]-thymidine (specific activity 6.7 Ci/mmol, DuPont NEN) for 3 hours and thymidine incorporation into DNA was determined by liquid scintillation counting.

FIG. 5 shows the incorporation of $^3$H-thymidine into DNA in human fibroblasts. Cells were serum-starved and treated with buffer only (samples 1 and 2) or with PDGF (samples 3 and 4). Data points are the average of duplicate samples.

As shown in FIG. 5, the foreskin fibroblasts responded to PDGF with about 2.3-fold higher DNA synthesis when plated on vitronectin than they did on collagen (compare column 3 with column 4). In parallel attachment assays, performed as described in Pytela et al., *PNAS* USA 82:5766 (1985), no differences were observed between human foreskin fibroblast adhesion to vitronectin and collagen. Because cell adhesion to vitronectin was completely inhibited by a polyclonal anti-$\alpha_v\beta_3$ antibody or a monoclonal $\alpha_v\beta_3$ antibody, the observed adhesion of the cells on vitronectin is solely mediated by the $\alpha_v\beta_3$ integrin. The antibodies mentioned above did not have any effect on cell adhesion to collagen, demonstrating that the $\alpha_v\beta_3$ integrin does not mediate this adhesion. There is thus an increase in the PDGF-responsiveness of human foreskin fibroblasts in the presence of the $\alpha_v\beta_3$ integrin binding to its ligand. This effect may be mediated by the $\alpha_v\beta_3$-associated 190 kDa protein described by Bartfeld et al. *J Biol. Chem.* 268:17270 (1993) which might be analogous to IRS-1 in insulin-stimulated cells.

EXAMPLE V

Effect of Ligand Binding of the $\alpha_v\beta_3$ Integrin on DNA Synthesis in EGF-Stimulated Rat-1 Cells This example demonstrates the effect of the ligand binding of the $\alpha_v\beta_3$ integrin on Epidermal growth factor (EGF)-stimulated cell proliferation measured by DNA synthesis in Rat-1 fibroblast cells.

Rat-1 cells were plated at $1\times10^5$ cells/well on 24-well plates that had been coated for 12 hours either with 20 µg/ml of vitronectin or 20 µg/ml of type I collagen. Cells were incubated for 36 hours in Dulbecco's modified Eagle's medium containing 0.1% bovine serum albumin followed by addition of buffer or 40 ng/ml EGF (Boehringer Mannheim). After 15 hours, the cells were pulse-labeled with 1 µCi/ml [$^3$H]-thymidine (specific activity 6.7 Ci/mmol, DuPont NEN) for 3 hours and thymidine incorporation into DNA was determined by liquid scintillation counting.

Figure 6:
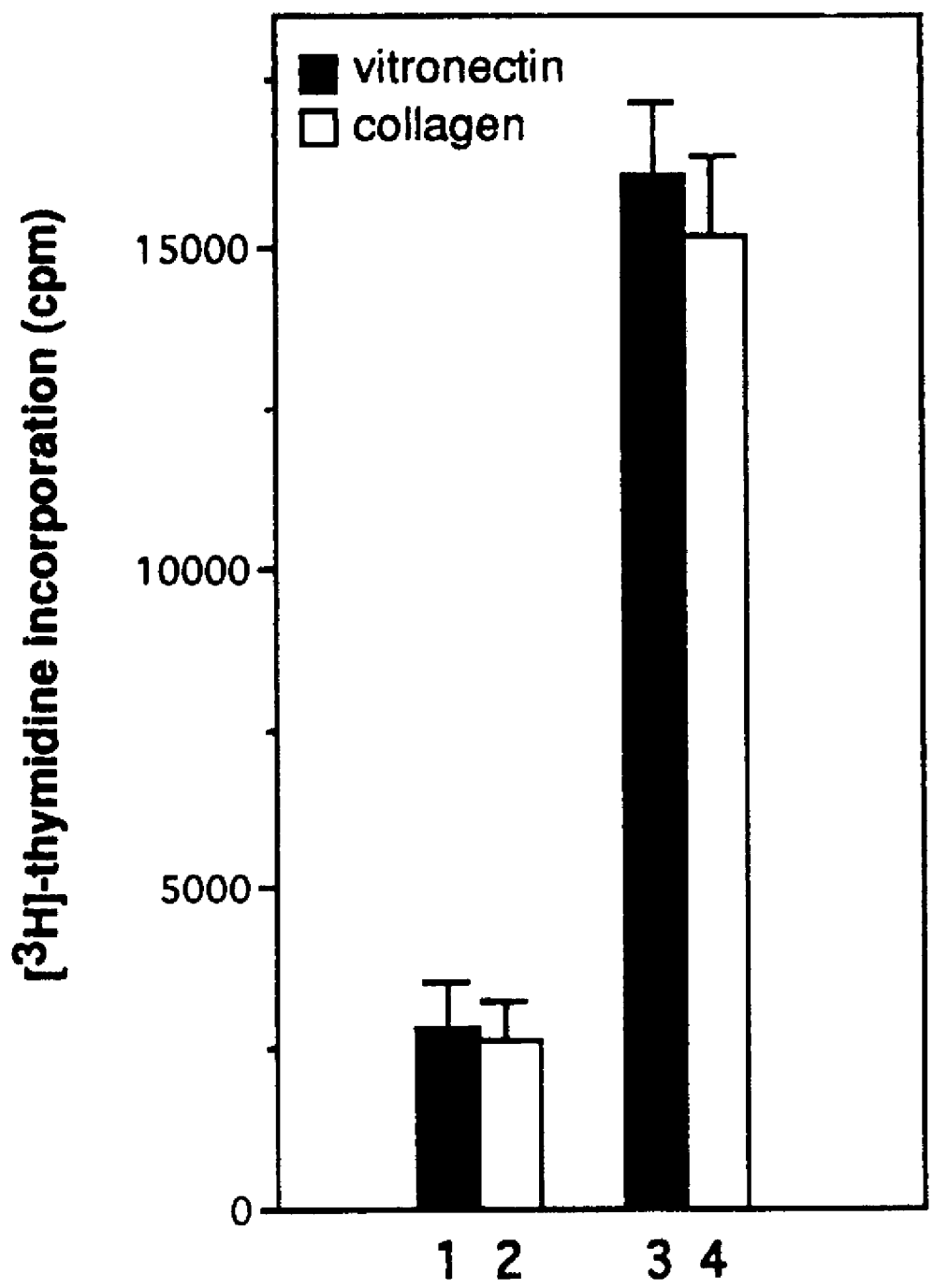
FIG. 6 shows DNA synthesis in Rat-1 cells plated on vitronectin or collagen with (columns 3 and 4) or without (columns 1 and 2) EGF treatment.

The incorporation of $^3$H-thymidine into DNA in Rat-1 cells is shown in FIG. 6. After being serum-starved, the cells were treated with buffer only (samples 1 and 2) or with EGF (samples 3 and 4). Data points are the average of triplicate samples.

As demonstrated in FIG. 6, the Rat-1 cells showed the same response to EGF whether plated on vitronectin or collagen. In parallel attachment assays, performed as in Pytela et al., *PNAS* USA 82:5766 (1985), no differences were observed between rat-1 cell adhesion to vitronectin and collagen. Because cell adhesion to vitronectin was completely inhibited by a polyclonal anti-$\alpha_v\beta_3$ antibody, the observed adhesion of the cells on vitronectin is solely mediated by the $\alpha_v\beta_3$ integrin. The antibodies did not have any effect on cell adhesion to collagen, demonstrating that the $\alpha_v\beta_3$ integrin does not mediate this adhesion. The EGF-responsiveness of Rat-1 cells therefore is not dependent on whether the $\alpha_v\beta_3$ integrin binds to its ligand.

Although this invention has been described with reference to the presently preferred embodiments, it is understood that various modifications can be made without departing from the spirit of the invention. According, the invention is limited only by the following claims.

We claim:

1. A method of treating a wound comprising placing into the wound a composition comprising a substantially purified first ligand to an $\alpha_v\beta_3$ integrin and a substantially purified second ligand selected from the group consisting of a ligand to a PDGF receptor, a ligand to an insulin receptor, a ligand to an IL-4 receptor, and a ligand to an insulin-like growth factor receptor, wherein said first ligand and said second ligand are incorporated within a matrix, and wherein the combination of said first ligand and said second ligand results in a synergistic effect on cell proliferation or cell migration.

2. A method of treating a wound comprising placing into the wound a composition comprising
    (a) a first ligand to an $\alpha_v\beta_3$ integrin consisting of G(dR)(dR)(dR)(dR)(dR)GGG(dR)GDSPASSK (Seq ID No. 1);
    (b) a matrix consisting of hyaluronic acid conjugated to said first ligand to form a synthetic matrix semi-gel; and
    (c) a second ligand associated with said synthetic matrix semi-gel and selected from the group consisting of insulin, insulin-like growth factor, IL-4, PDGF and biologically active analogs thereof.

3. A method of inducing or enhancing tissue regeneration comprising placing into a wound a composition comprising a substantially purified first ligand to an $\alpha_v\beta_3$ integrin and a substantially purified second ligand selected from the group consisting of a ligand to a PDGF receptor, a ligand to an insulin receptor, a ligand to an IL-4 receptor, and a ligand to an insulin-like growth factor receptor, wherein said first ligand and said second ligand are incorporated within a matrix, and wherein the combination of said first ligand and said second ligand results in a synergistic effect on cell proliferation or cell migration.

4. A method of inducing or enhancing tissue regeneration comprising placing into a wound a composition comprising
  (a) a first ligand to an $\alpha_V\beta_3$ integrin consisting of G(dR)(dR)(dR)(dR)(dR)GGG(dR)GDSPASSK (Seq ID No. 1);
  (b) a matrix consisting of hyaluronic acid conjugated to said first ligand to form a synthetic matrix semi-gel; and
  (c) a second ligand associated with said synthetic matrix semi-gel and selected from the group consisting of insulin, insulin-like growth factor, IL-4, PDGF and biologically active analogs thereof.

* * * * *

UNITED STATES PATENT AND TRADEMARK OFFICE
CERTIFICATE OF CORRECTION

PATENT NO. : 5,830,504
DATED : November 3, 1998
INVENTOR(S) : Vuori et al.

Page 1 of 1

It is certified that error appears in the above-identified patent and that said Letters Patent is hereby corrected as shown below:

Column 8,
Line 18, please delete "herrin," and replace with -- herein, --.

Column 15,
Line 45, please delete "and $\beta_2$-expressing" and replace with -- and $\beta_1$-expressing --.

Column 16,
Line 20, please delete "For" and replace with -- for --.

Column 17,
Line 28, please delete "$\alpha_v\beta_1$" and replace with -- $\alpha_v\beta_3$ --.

Column 18,
Line 56, please delete "According," and replace with -- Accordingly, --.

Signed and Sealed this

Twenty-seventh Day of November, 2001

Attest:

*Nicholas P. Godici*

NICHOLAS P. GODICI
*Attesting Officer*    *Acting Director of the United States Patent and Trademark Office*